US008013129B2

(12) United States Patent
Tsai et al.

(10) Patent No.: US 8,013,129 B2
(45) Date of Patent: Sep. 6, 2011

(54) PROTEIN SEPARATION DEVICE

(75) Inventors: Heng Hang Tsai, Singapore (SG);
Hon-Chiu Eastwood Leung, Houston, TX (US)

(73) Assignee: Agency for Science, Technology and Research, Centros (SG)

( * ) Notice: Subject to any disclaimer, the term of this patent is extended or adjusted under 35 U.S.C. 154(b) by 571 days.

(21) Appl. No.: 10/583,179

(22) PCT Filed: Dec. 17, 2004

(86) PCT No.: PCT/SG2004/000417
§ 371 (c)(1),
(2), (4) Date: Aug. 25, 2008

(87) PCT Pub. No.: WO2005/058949
PCT Pub. Date: Jun. 30, 2005

(65) Prior Publication Data
US 2009/0093061 A1    Apr. 9, 2009

Related U.S. Application Data

(60) Provisional application No. 60/530,608, filed on Dec. 19, 2003.

(51) Int. Cl.
*A23J 1/00*      (2006.01)
*G01N 33/00*     (2006.01)
*B01D 11/02*     (2006.01)

(52) U.S. Cl. ............... 530/412; 435/309.1; 422/261; 436/86

(58) Field of Classification Search .................. None
See application file for complete search history.

(56) References Cited

U.S. PATENT DOCUMENTS
2002/0142369 A1*  10/2002  Fersht ................ 435/68.1

FOREIGN PATENT DOCUMENTS
| JP | 07-048398 | 2/1995 |
| WO | WO 02/083725 A1 | 10/2002 |
| WO | WO 03/048783 A1 | 6/2003 |
| WO | WO 03/061570 A2 | 7/2003 |

OTHER PUBLICATIONS

Agard, D.A., "To fold or not to fold", Science, (1993) p. 1903-1904, vol. 260.
Altschul, S.F., et al., "Basic Local Alignment Search Tool", J. Mol. Biol., (1990) p. 403-410, vol. 215.
Ausubel, et al. (eds), Current Protocols in Molecular Biology, (1989) p. 2.10.3, vol. 1, Green Publishing Associates, Inc. and John Wiley & Sons, Inc., New York.
Bhutani, N., et al., "Chaperonins as protein-folding machines", Current Science, (2002) p. 1337-1351, vol. 83, No. 11.

(Continued)

*Primary Examiner* — Krishnan S Menon
*Assistant Examiner* — Dirk Bass
(74) *Attorney, Agent, or Firm* — Barbara A. Wrigley; Oppenheimer Wolff & Donnelly, LLP

(57) ABSTRACT

The invention provides a protein separation device comprising a chaperone protein immobilized on a substrate. In one embodiment, the chaperone protein is an Hsp60 chaperone, preferably a group one chaperone, preferably GroEL. The invention also provides a method for isolating a protein from a biological sample using a protein separation device of the invention.

30 Claims, 12 Drawing Sheets

OTHER PUBLICATIONS

Brazil, B.T., et al., "Model Peptide Studies Demonstrate That Amphipathic Secondary Structures Can Be Recognized by the Chaperonin GroEL (cpn60)", J. Biol. Chem., (1997) p. 5105-5111, vol. 272, No. 8.

Bukau, B., et al., "The Hsp70 and Hsp60 Chaperone Machines", Cell, (1998) p. 351-366, vol. 92.

Chatellier, J., et al., "GroEL Recognises Sequential and Non-sequential Linear Structural Motifs Compatible with Extended β-Strands and α-Helices", J. Mol. Biol., (1999) p. 163-172, vol. 292.

Chaudhuri, T.K., et al., "GroEL/GroES-Mediated Folding of a Protein Too Large to Be Encapsulated", Cell, (2001) p. 235-246, vol. 107.

DebBurman, S.K., et al., "Chaperone-supervised conversion of prion protein to its protease-resistant form", Proc. Natl. Acad. Sci. U.S.A., (1997) p. 13938-13943, vol. 94. No. 25.

Erbse, A., et al., "A folding machine for many but a master of none", Nature Structural Biology, (2003) p. 84-86, vol. 10, No. 2.

Geminard, et al., "Characteristics of the interaction between Hsc70 and the transferrin receptor in exosomes released during reticulocyte maturation", J. Biological Chem., (2001) p. 9910-9916, vol. 276.

Hartl, F.U., et al., "Molecular Chaperones in the Cytosol: from Nascent Chain to Folded Protein", Science, (2002) p. 1852-1858, vol. 295.

Hemmingsen, S.M., "What is a chaperonin?", Nature, (1992) p. 650, vol. 357, No. 6380.

Houry, W.A., "Mechanism of substrate recognition by the chaperonin GroEL", Biochem. Cell Biol., (2001) p. 569-577, vol. 79, © 2001 NRC Canada.

Hynes, et al., "Individual subunits of the eukaryotic cytosolic chaperonin mediate interactions with binding sites located on subdomains of β-actin", J. Biological Chem., (2000) p. 18965-18994, vol. 275.

Kinbara, K., et al., "RAS GTPases: Integrins' Friends or Foes?", Nature Reviews: Molecular Cell Biology, (2003) p. 767-776, vol. 4.

Klumpp, M., et al., "Structure of the Substrate Binding Domain of the Thermosome, an Archaeal Group II Chaperonin", Cell, (1997) p. 263-270, vol. 91.

Nadeau, et al., "Hsp90 chaperonins possess ATPase activity and bind heat shock transcription factors and peptidyl propyl isomerases", J. Biological Chem., (1993) p. 1479-1487, vol. 268.

Nam, et al., "Affinity Purification and characterization of the *Escherichia coli* molecular chaperones", Protein Expression and Purification, (2002) p. 282-291, vol. 24.

Needleman, et al., "A General Method Applicable to the Search for Similarities in the Amino Acid Sequence of Two Proteins", J. Mol. Biol., (1970) p. 443-453, vol. 48.

Nielsen, K.L., et al., "A Single-Ring Mitochondrial Chaperonin (Hsp60-Hsp10) Can Substitute for GroEL-GroES In Vivo", Journal of Bacteriology, (1999) p. 5871-5875, vol. 181, No. 18.

Pearson, W.R., et al., "Improved tools for biological sequence comparison", Proc. Natl. Acad. Sci. USA, (1988) p. 2444-2448, vol. 85.

Sakikawa, C., et al., "On the Maximum Size of Proteins to Stay and Fold in the Cavity of GroEL underneath GroES", J. Biol. Chem., (1999) p. 21251-21256, vol. 274, No. 30, Issue of Jul. 23.

Seale, J.W., et al., "Preformed GroES Oligomers Are Not Required as Functional Cochaperonins", Journal of Protein Chemistry, (1997) p. 661-668, vol. 16, No. 7.

Smith, et al., "Comparison of Biosequences", Adv. Appl. Math., (1981) p. 482-489, vol. 2.

Staniford, R.A., et al., "The stability and hydrophobicity of cytosolic and mitochondrial malate dehydrogenases and their relation to chaperonin-assisted folding", FEBS Letters, (1994) p. 129-135, vol. 344.

Straub, et al., "Genotyping Cryptosporidium parvum with an hsp 70 single-nucleotide polymorphism microarray", Applied and Environmental Microbiology, (2002) p. 1817-1826, vol. 68.

Taguchi, H., et al., "Single-molecule observation of protein-protein interactions in the chaperonin system", Nature Biotechnology, (2001) p. 861-865, vol. 19.

Carrascosa, J. L., et al, "Structural comparison of prokaryotic and eukaryotic chaperonins", Micron., (2001) p. 43-50, vol. 32, No. 1.

Dong, X-Y., et al., "Lysozyme refolding with immobilized GroEL Column chromatography", Journal of Chromatography, Elsevier Science Publishers B.V. Amsterdam, NL, (2000) p. 197-204, vol. 878, No. 2.

Gao, Y-G., et al., "On-column refolding of recombinant human interferon-gamma with an immobilized chaperone fragment", Biotechnology Progress, (2003) p. 915-920, vol. 19, No. 3.

Preston, N.S., et al., "The production and characterisation of an immobilised chaperonin system", Biochimica. et Biophysica. Acta., (1999) p. 99-109, vol. 1426, No. 1.

Sun, Z., et al., "Isolation and Characterisation of Mutants of GroEL that are Fully Functional as Single Rings", Journal of Molecular Biology, London, GB (2003) p. 715-728, vol. 332, No. 3.

Tell, et al. "Comparison of four rapid DNA extraction techniques for conventional polymerase chain reaction testing of three mycobacterium spp. that affects birds", Avian Diseases, (Oct. 2003) p. 1486-1490, Vol. 47.

Tijssen, "Overview of principles of hybridization and the strategy of nucleic acid probe assays", Laboratory Techniques in Biochemistry and Molecular Biology—Hybridization with Nucleic Acid Probes, (1993) Part I, Chapter 2, Elsevier, New York.

Wang, Z.., et al., "Basis of Substrate Binding by the Chaperonin GroEL", Biochem., (1999) p. 12537-12546, vol. 38.

Xu, Z., et al., "The crystal structure of the asymmetric GroEL-GroES-(ADP)$_7$ chaperonin complex", Nature, (1997) p. 741-750, vol. 388.

Ball, H.L. et al., "Application of Reversible Biotinylated Label for Directed Immobilization of Synthetic Peptides and Proteins: Isolation of Ligates from Crude Cell Lysates", Journal of Peptide Science, 1997, vol. 3, pp. 252-260.

Evers, M.E. et al., "Affinity Purification of Molecular Chaperones of the Yeast Hansenula Polymorpha Using Immbolized Denatured Alcohol Oxidase", FEBS LETT., 1993, vol. 321, No. 1, pp. 32-36, Federation of European Biochemical Societies.

Nielsen, E., et al., "Stable association of chloroplastic precursors with protein translocation complexes that contain proteins from both envelope membranes and a stromal Hsp100 molecular chaperone", The EMBO (European Molecular Biology Organization) Journal, (1997) XP-002438870, pp. 935-946, vol. 16, No. 5.

Office Action dated Jul. 20, 2010, issued by the Japanese Patent Office, regarding patent application serial No. 2006-545304.

Viitanen, Paul V., et al.; "Purified Chaperonin 60 (groEL) Interacts With the Nonnative States of a Multitude of *Escherichia coli* Proteins"; Protein Science; vol. 1; 1992; pp. 363-369; Cambridge University Press, USA.

Phadtare, Sangita, et al.; "Refolding and Release of Tubulins by a Functional Immobilized groEL Column"; BioChimica et Biophysics Acta 1208; 1994; pp. 189-192; Elsevier, USA.

Nieba, Lars, et al.; "BIACORE Analysis of Histidine-Tagged Proteins Using a Chelating NTA Sensor Chip"; Analytical Biochemistry; vol. 252 / Article AB972326; 1997; pp. 217-228; Academic Press, Sweden.

* cited by examiner

| | |
|---|---|
| 1 | ATGGCAGCTAAAGACGTAAAATTCGGTAACGACGCTCGTGTGAAAATGCTGCGCGGCGTA |
| 1 | METAlaAlaLysAspValLysPheGlyAsnAspAlaArgValLysMETLeuArgGlyVal |
| 61 | AACGTACTGGCAGATGCAGTGAAAGTTACCCTCGGTCCGAAAGGCCGTAACGTAGTTCTG |
| 21 | AsnValLeuAlaAspAlaValLysValThrLeuGlyProLysGlyArgAsnValValLeu |
| 121 | GATAAATCTTTCGGTGCACCGACCATCACCAAAGATGGTGTTTCCGTTGCTCGTGAAATC |
| 41 | AspLysSerPheGlyAlaProThrIleThrLysAspGlyValSerValAlaArgGluIle |
| 181 | GAACTGGAAGACAAGTTCGAAAACATGGGTGCGCAGATGGTGAAAGAAGTTGCCTCTAAA |
| 61 | GluLeuGluAspLysPheGluAsnMETGlyAlaGlnMETValLysGluValAlaSerLys |
| 241 | GCGAACGACGCTGCAGGCGACGGTACCACCACTGCAACCGTACTGGCTCAGGCTATCATC |
| 81 | AlaAsnAspAlaAlaGlyAspGlyThrThrThrAlaThrValLeuAlaGlnAlaIleIle |
| 301 | ACTGAAGGTCTGAAAGCTGTTGCTGCGGGCATGAACCCGATGGACCTGAAACGTGGTATC |
| 101 | ThrGluGlyLeuLysAlaValAlaAlaGlyMETAsnProMETAspLeuLysArgGlyIle |
| 361 | GACAAAGCTGTTACCGCTGCAGTTGAAGAACTGAAAGCGCTGTCCGTACCGTGCTCTGAC |
| 121 | AspLysAlaValThrAlaAlaValGluGluLeuLysAlaLeuSerValProCysSerAsp |
| 421 | TCTAAAGCGATTGCTCAGGTTGGTACTATCTCCGCTAACTCCGACGAAACCGTAGGTAAA |
| 141 | SerLysAlaIleAlaGlnValGlyThrIleSerAlaAsnSerAspGluThrValGlyLys |
| 481 | CTGATCGCTGAAGCGATGGACAAAGTCGGTAAAGAAGGCGTTATCACCGTTGAAGACGGT |
| 161 | LeuIleAlaGluAlaMETAspLysValGlyLysGluGlyValIleThrValGluAspGly |
| 541 | ACCGGTCTGCAGGACGAACTGGACGTGGTTGAAGGTATGCAGTTCGACCGTGGCTACCTG |
| 181 | ThrGlyLeuGlnAspGluLeuAspValValGluGlyMETGlnPheAspArgGlyTyrLeu |
| 601 | TCTCCTTACTTCATCAACAAGCCGGAAACTGGCGCAGTAGAACTGGAAAGCCCGTTCATC |
| 201 | SerProTyrPheIleAsnLysProGluThrGlyAlaValGluLeuGluSerProPheIle |
| 661 | CTGCTGGCTGACAAGAAAATCTCCAACATCCGCGAAATGCTGCCGGTTCTGGAAGCCGTT |
| 221 | LeuLeuAlaAspLysLysIleSerAsnIleArgGluMETLeuProValLeuGluAlaVal |
| 721 | GCCAAAGCAGGCAAACCGCTGCTGATCATCGCTGAAGATGTAGAAGGCGAAGCGCTGGCA |
| 241 | AlaLysAlaGlyLysProLeuLeuIleIleAlaGluAspValGluGlyGluAlaLeuAla |
| 781 | ACTCTGGTTGTTAACACCATGCGTGGCATCGTGAAAGTTGCTGCAGTTAAAGCTCCGGGC |
| 261 | ThrLeuValValAsnThrMETArgGlyIleValLysValAlaAlaValLysAlaProGly |
| 841 | TTCGGCGATCGTCGTAAAGCTATGCTGCAGGATATCGCAACCCTGACTGGCGGTACCGTA |
| 281 | PheGlyAspArgArgLysAlaMETLeuGlnAspIleAlaThrLeuThrGlyGlyThrVal |
| 901 | ATCTCTGAAGAGATCGGTATGGAGCTGGAAAAAGCAACCCTGGAAGACCTGGGTCAGGCT |
| 301 | IleSerGluGluIleGlyMETGluLeuGluLysAlaThrLeuGluAspLeuGlyGlnAla |
| 961 | AAACGCGTTGTGATCAACAAAGACACCACCACCATCATCGATGGCGTGGGCGAAGAAGCT |
| 321 | LysArgValValIleAsnLysAspThrThrThrIleIleAspGlyValGlyGluGluAla |
| 1021 | GCAATCCAGGGCCGTGTTGCTCAGATCCGTCAGCAGATTGAAGAAGCAACTTCTGACTAC |
| 341 | AlaIleGlnGlyArgValAlaGlnIleArgGlnGlnIleGluGluAlaThrSerAspTyr |

FIG. 1A

```
1081    GACCGTGAAAAACTGCAGGAGCGCGTAGCGAAACTGGCAGGCGGCGTTGCAGTTATCAAA
361     AspArgGluLysLeuGlnGluArgValAlaLysLeuAlaGlyGlyValAlaValIleLys
1141    GTAGGTGCTGCTACCGAAGTTGAAATGAAAGAGAAAAAAGCACGCGTTGAAGACGCCCTG
381     ValGlyAlaAlaThrGluValGluMETLysGluLysLysAlaArgValGluAspAlaLeu
1201    CACGCGACCCGTGCTGCGGTAGAAGAAGGCGTGGTTGCTGGTGGTGGTGTTGCGCTGATC
401     HisAlaThrArgAlaAlaValGluGluGlyValValAlaGlyGlyGlyValAlaLeuIle

1261    CGCGTAGCGTCTAAACTGGCTGACCTGCGTGGTCAGAACGAAGACCAGAACGTGGGTATC
421     ArgValAlaSerLysLeuAlaAspLeuArgGlyGlnAsnGluAspGlnAsnValGlyIle

1321    AAAGTTGCACTGCGTGCAATGGAAGCTCCGCTGCGTCAGATCGTCCTGAACTGCGGCGAA
441     LysValAlaLeuArgAlaMETGluAlaProLeuArgGlnIleValLeuAsnCysGlyGlu

1381    GAACCGTCTGTTGTTGCTAACACCGTTAAAGGCGGCGACGGCAACTACGGTTACAACGCA
461     GluProSerValValAlaAsnThrValLysGlyGlyAspGlyAsnTyrGlyTyrAsnAla

1441    GCAACCGAAGAATACGGCAACATGATCGACATGGGTATCCTGGACCCAACCAAAGTAACC
481     AlaThrGluGluTyrGlyAsnMETIleAspMETGlyIleLeuAspProThrLysValThr

1501    CGTTCTGCTCTGCAGTACGCGGCTTCTGTGGCTGGCCTGATGATCACCACCGAATGCATG
501     ArgSerAlaLeuGlnTyrAlaAlaSerValAlaGlyLeuMETIleThrThrGluCysMET

1561    GTTACCGACCTGCCGAAAAACGATGCAGCTGACTTAGGCGCTGCTGGCGGCATGGGTGGC
521     ValThrAspLeuProLysAsnAspAlaAlaAspLeuGlyAlaAlaGlyGlyMETGlyGly

1621    ATGGGTGGCATGGGCGGCATGATGTAA
541     METGlyGlyMETGlyGlyMETMET***
```

FIG. 1B

```
  1    ATGGCAGCTAAAGACGTAAAATTCGGTAACGACGCTCGTGTGAAAATGCTGCGCGGCGTA
  1    METAlaAlaLysAspValLysPheGlyAsnAspAlaArgValLysMETLeuArgGlyVal

61    AACGTACTGGCAGATGCAGTGAAAGTTACCCTCGGTCCGAAAGGCCGTAACGTAGTTCTG
 21    AsnValLeuAlaAspAlaValLysValThrLeuGlyProLysGlyArgAsnValValLeu

121    GATAAATCTTTCGGTGCACCGACCATCACCAAAGATGGTGTTTCCGTTGCTCGTGAAATC
 41    AspLysSerPheGlyAlaProThrIleThrLysAspGlyValSerValAlaArgGluIle

181    GAACTGGAAGACAAGTTCGAAAACATGGGTGCGCAGATGGTGAAAGAAGTTGCCTCTAAA
 61    GluLeuGluAspLysPheGluAsnMETGlyAlaGlnMETValLysGluValAlaSerLys

241    GCGAACGACGCTGCAGGCGACGGTACCACCACTGCAACCGTACTGGCTCAGGCTATCATC
 81    AlaAsnAspAlaAlaGlyAspGlyThrThrThrAlaThrValLeuAlaGlnAlaIleIle

301    ACTGAAGGTCTGAAAGCTGTTGCTGCGGGCATGAACCCGATGGACCTGAAACGTGGTATC
101    ThrGluGlyLeuLysAlaValAlaAlaGlyMETAsnProMETAspLeuLysArgGlyIle

361    GACAAAGCTGTTACCGCTGCAGTTGAAGAACTGAAAGCGCTGTCCGTACCGTGCTCTGAC
121    AspLysAlaValThrAlaAlaValGluGluLeuLysAlaLeuSerValProCysSerAsp

421    TCTAAAGCGATTGCTCAGGTTGGTACTATCTCCGCTAACTCCGACGAAACCGTAGGTAAA
141    SerLysAlaIleAlaGlnValGlyThrIleSerAlaAsnSerAspGluThrValGlyLys

481    CTGATCGCTGAAGCGATGGACAAAGTCGGTAAAGAAGGCGTTATCACCGTTGAAGACGGT
161    LeuIleAlaGluAlaMETAspLysValGlyLysGluGlyValIleThrValGluAspGly

541    ACCGGTCTGCAGGACGAACTGGACGTGGTTGAAGGTATGCAGTTCGACCGTGGCTACCTG
181    ThrGlyLeuGlnAspGluLeuAspValValGluGlyMETGlnPheAspArgGlyTyrLeu

601    TCTCCTTACTTCATCAACAAGCCGGAAACTGGCGCAGTAGAACTGGAAAGCCCGTTCATC
201    SerProTyrPheIleAsnLysProGluThrGlyAlaValGluLeuGluSerProPheIle

661    CTGCTGGCTGACAAGAAAATCTCCAACATCCGCGAAATGCTGCCGGTTCTGGAAGCCGTT
221    LeuLeuAlaAspLysLysIleSerAsnIleArgGluMETLeuProValLeuGluAlaVal

721    GCCAAAGCAGGCAAACCGCTGCTGATCATCGCTGAAGATGTAGAAGGCGAAGCGCTGGCA
241    AlaLysAlaGlyLysProLeuLeuIleIleAlaGluAspValGluGlyGluAlaLeuAla

781    ACTCTGGTTGTTAACACCATGCGTGGCATCGTGAAAGTTGCTGCAGTTAAAGCTCCGGGC
261    ThrLeuValValAsnThrMETArgGlyIleValLysValAlaAlaValLysAlaProGly

841    TTCGGCGATCGTCGTAAAGCTATGCTGCAGGATATCGCAACCCTGACTGGCGGTACCGTA
281    PheGlyAspArgArgLysAlaMETLeuGlnAspIleAlaThrLeuThrGlyGlyThrVal

901    ATCTCTGAAGAGATCGGTATGGAGCTGGAAAAAGCAACCCTGGAAGACCTGGGTCAGGCT
301    IleSerGluGluIleGlyMETGluLeuGluLysAlaThrLeuGluAspLeuGlyGlnAla

961    AAACGCGTTGTGATCAACAAAGACACCACCACCATCATCGATGGCGTGGGCGAAGAAGCT
321    LysArgValValIleAsnLysAspThrThrThrIleIleAspGlyValGlyGluGluAla
```

FIG. 2A

```
1021      GCAATCCAGGGCCGTGTTGCTCAGATCCGTCAGCAGATTGAAGAAGCAACTTCTGACTAC
 341      AlaIleGlnGlyArgValAlaGlnIleArgGlnGlnIleGluGluAlaThrSerAspTyr

1081      GACCGTGAAAAACTGCAGGAGCGCGTAGCGAAACTGGCAGGCGGCGTTGCAGTTATCAAA
 361      AspArgGluLysLeuGlnGluArgValAlaLysLeuAlaGlyGlyValAlaValIleLys

1141      GTAGGTGCTGCTACCGAAGTTGAAATGAAAGAGAAAAAAGCACGCGTTGAAGACGCCCTG
 381      ValGlyAlaAlaThrGluValGluMETLysGluLysLysAlaArgValGluAspAlaLeu

1201      CACGCGACCCGTGCTGCGGTAGAAGAAGGCGTGGTTGCTGGTGGTGGTGTTGCGCTGATC
 401      HisAlaThrArgAlaAlaValGluGluGlyValValAlaGlyGlyGlyValAlaLeuIle

1261      CGCGTAGCGTCTAAACTGGCTGACCTGCGTGGTCAGAACGAAGACCAGAACGTGGGTATC
 421      ArgValAlaSerLysLeuAlaAspLeuArgGlyGlnAsnGluAspGlnAsnValGlyIle

1321      AAAGTTGCACTGCGTGCAATGGAAGCTCCGCTGCGTCAGATCGTCCTGAACTGCGGCGAA
 441      LysValAlaLeuArgAlaMETGluAlaProLeuArgGlnIleValLeuAsnCysGlyGlu

1381      GAACCGTCTGTTGTTGCTAACACCGTTAAAGGCGGCGACGGCAACTACGGTTACAACGCA
 461      GluProSerValValAlaAsnThrValLysGlyGlyAspGlyAsnTyrGlyTyrAsnAla

1441      GCAACCGAAGAATACGGCAACATGATCTGCATGGGTATCCTGGACCCAACCAAAGTAACC
 481      AlaThrGluGluTyrGlyAsnMETIleCysMETGlyIleLeuAspProThrLysValThr

1501      CGTTCTGCTCTGCAGTACGCGGCTTCTGTGGCTGGCCTGATGATCACCACCGAATGCATG
 501      ArgSerAlaLeuGlnTyrAlaAlaSerValAlaGlyLeuMETIleThrThrGluCysMET

1561      GTTACCGACCTGCCGAAAAACGATGCAGCTGACTTAGGCGCTGCTGGCGGCATGGGTGGC
 521      ValThrAspLeuProLysAsnAspAlaAlaAspLeuGlyAlaAlaGlyGlyMETGlyGly

1621      ATGGGTGGCATGGGCGGCATGATGTAA
 541      METGlyGlyMETGlyGlyMETMET***
```

FIG. 2B

| | |
|---|---|
| 1 | ATGGCAGCTAAAGACGTAAAATTCGGTAACGACGCTCGTGTGAAAATGCTGCGCGGCGTA |
| 1 | METAlaAlaLysAspValLysPheGlyAsnAspAlaArgValLysMETLeuArgGlyVal |
| 61 | AACGTACTGGCAGATGCAGTGAAAGTTACCCTCGGTCCAAAAGGCCGTAACGTAGTTCTG |
| 21 | AsnValLeuAlaAspAlaValLysValThrLeuGlyProLysGlyArgAsnValValLeu |
| 121 | GATAAATCTTTCGGTGCACCGACCATCACCAAAGATGGTGTTTCCGTTGCTCGTGAAATC |
| 41 | AspLysSerPheGlyAlaProThrIleThrLysAspGlyValSerValAlaArgGluIle |
| 181 | GAACTGGAAGACAAGTTCGAAAATATGGGTGCGCAGATGGTGAAAGAAGTTGCCTCTAAA |
| 61 | GluLeuGluAspLysPheGluAsnMETGlyAlaGlnMETValLysGluValAlaSerLys |
| 241 | GCAAACGACGCTGCAGGCGACGGTACCACCACTGCAACCGTACTGGCTCAGGCTATCATC |
| 81 | AlaAsnAspAlaAlaGlyAspGlyThrThrThrAlaThrValLeuAlaGlnAlaIleIle |
| 301 | ACTGAAGGTCTGAAAGCTGTTGCTGCGGGCATGAACCCGATGGACCTGAAACGTGGTATC |
| 101 | ThrGluGlyLeuLysAlaValAlaAlaGlyMETAsnProMETAspLeuLysArgGlyIle |
| 361 | GACAAAGCGGTTACCGTTGCAGTTGAAGAACTGAAAGCGCTGTCCGTACCATGCTCTGAC |
| 121 | AspLysAlaValThrValAlaValGluGluLeuLysAlaLeuSerValProCysSerAsp |
| 421 | TCTAAAGCGATTGCTCAGGTTGGTACCATCTCCGCTAACTCCGACGAAACCGTAGGTAAA |
| 141 | SerLysAlaIleAlaGlnValGlyThrIleSerAlaAsnSerAspGluThrValGlyLys |
| 481 | CTGATCGCTGAAGCGATGGACAAAGTCGGTAAAGAAGGCGTTATCACCGTTGAAGACGGT |
| 161 | LeuIleAlaGluAlaMETAspLysValGlyLysGluGlyValIleThrValGluAspGly |
| 541 | ACCGGTCTGCAGGACGAACTGGACGTGGTTGAAGGTATGCAGTTCGACCGTGGCTACCGT |
| 181 | ThrGlyLeuGlnAspGluLeuAspValValGluGlyMETGlnPheAspArgGlyTyrArg |
| 601 | TATGATTACTTCATCAACAAGCCGGAAACTGGCGCAGTAGAACTGGAAAGCCCGTTCATC |
| 201 | TyrAspTyrPheIleAsnLysProGluThrGlyAlaValGluLeuGluSerProPheIle |
| 661 | CTGCTGGCTGACAAGAAAATCTCCAACATCCGCGAAATGCTGCCGGTTCTGGAAGCTGTT |
| 221 | LeuLeuAlaAspLysLysIleSerAsnIleArgGluMETLeuProValLeuGluAlaVal |
| 721 | GCCAAAGCAGGCAAACCGCTGCTGATCATCGCTGAAGATGTAGAAGGCGAAGCGCTGGCA |
| 241 | AlaLysAlaGlyLysProLeuLeuIleIleAlaGluAspValGluGlyGluAlaLeuAla |
| 781 | ACTCTGGTTGTTAACACCATGCGTGGCATCGTGAAAGTCGCTGCGGTTAAAGCACCGGGC |
| 261 | ThrLeuValValAsnThrMETArgGlyIleValLysValAlaAlaValLysAlaProGly |
| 841 | TTCGGCGATCGTCGTAAAGCTATGCTGCAGGATATCGCAACCCTGACTGGCGGTACCGTG |
| 281 | PheGlyAspArgArgLysAlaMETLeuGlnAspIleAlaThrLeuThrGlyGlyThrVal |
| 901 | ATCTCTGAAGAGATCGGTATGGAGCTGGAAAAAGCAACCCTGGAAGACCTGGGTCAGGCT |
| 301 | IleSerGluGluIleGlyMETGluLeuGluLysAlaThrLeuGluAspLeuGlyGlnAla |
| 961 | AAACGTGTTGTGATCAACAAAGACACCACCACTATCATCGATGGCGTGGGTGAAGAAGCT |
| 321 | LysArgValValIleAsnLysAspThrThrThrIleIleAspGlyValGlyGluGluAla |
| 1021 | GCAATCCAGGGCCGTGTTGCTCAGATCCGTCAGCAGATTGAAGAAGCAACTTCTGACTAC |
| 341 | AlaIleGlnGlyArgValAlaGlnIleArgGlnGlnIleGluGluAlaThrSerAspTyr |

FIG. 3A

| | |
|---|---|
| 1081 | GACCGTGAAAAACTGCAGGAACGCGTAGCGAAACTGGCAGGCGGCGTTGCAGTTATCAAA |
| 361 | AspArgGluLysLeuGlnGluArgValAlaLysLeuAlaGlyGlyValAlaValIleLys |
| 1141 | GTGGGTGCTGCTACCGAAGTTGAAATGAAAGAGAAAAAAGCACGCGTTGAAGATGCCCTG |
| 381 | ValGlyAlaAlaThrGluValGluMETLysGluLysLysAlaArgValGluAspAlaLeu |
| 1201 | CACGCGACCCGTGCTGCGGTAGAAGAAGGCGTGGTTGCTGGTGGTGGTGTTGCGCTGATC |
| 401 | HisAlaThrArgAlaAlaValGluGluGlyValValAlaGlyGlyGlyValAlaLeuIle |
| 1261 | CGCGTAGCGTCTAAACTGGCTGACCTGCGTGGTCAGAACGAAGACCAGAACGTGGGTATC |
| 421 | ArgValAlaSerLysLeuAlaAspLeuArgGlyGlnAsnGluAspGlnAsnValGlyIle |
| 1321 | AAAGTTGCACTGCGTGCAATGGAAGCTCCGCTGCGTCAGATCGTATTGAACTGCGGCGAA |
| 441 | LysValAlaLeuArgAlaMETGluAlaProLeuArgGlnIleValLeuAsnCysGlyGlu |
| 1381 | GAACCGTCTGTTGTTGCTAACACCGTTAAAGGCGGCGACGGCAACTACGGTTACAACGCA |
| 461 | GluProSerValValAlaAsnThrValLysGlyGlyAspGlyAsnTyrGlyTyrAsnAla |
| 1441 | GCAACCGAAGAATACGGCAACATGATCTGCATGGGTATCCTGGATCCAACCAAAGTAACT |
| 481 | AlaThrGluGluTyrGlyAsnMETIleCysMETGlyIleLeuAspProThrLysValThr |
| 1501 | CGTTCTGCTCTGCAGTACGCAGCTTCTGTGGCTGGCCTGATGATCACCACCGAATGCATG |
| 501 | ArgSerAlaLeuGlnTyrAlaAlaSerValAlaGlyLeuMETIleThrThrGluCysMET |
| 1561 | GTTACCGACCTGCCGAAAAACGATGCAGCTGACTTAGGCGCTGCTGGCGGTATGGGCGGC |
| 521 | ValThrAspLeuProLysAsnAspAlaAlaAspLeuGlyAlaAlaGlyGlyMETGlyGly |
| 1621 | ATGGGTGGCATGGGCGGCATGATGTAA |
| 541 | METGlyGlyMETGlyGlyMETMET*** |

FIG. 3B

| | |
|---|---|
| 1 | ATGGCAGCTAAAGACGTAAAATTCGGTAACGACGCTCGTGTGAAAATGCTGCGCGGCGTA |
| 1 | METAlaAlaLysAspValLysPheGlyAsnAspAlaArgValLysMETLeuArgGlyVal |
| 61 | AACGTACTGGCAGATGCAGTGAAAGTTACCCTCGGTCCGAAAGGCCGTAACGTAGTTCTG |
| 21 | AsnValLeuAlaAspAlaValLysValThrLeuGlyProLysGlyArgAsnValValLeu |
| 121 | GATAAATCTTTCGGTGCACCGACCATCACCAAAGATGGTGTTTCCGTTGCTCGTGAAATC |
| 41 | AspLysSerPheGlyAlaProThrIleThrLysAspGlyValSerValAlaArgGluIle |
| 181 | GAACTGGAAGACAAGTTCGAAAACATGGGTGCGCAGATGGTGAAAGAAGTTGCCTCTAAA |
| 61 | GluLeuGluAspLysPheGluAsnMETGlyAlaGlnMETValLysGluValAlaSerLys |
| 241 | GCGAACGACGCTGCAGGCGACGGTACCACCACTGCAACCGTACTGGCTCAGGCTATCATC |
| 81 | AlaAsnAspAlaAlaGlyAspGlyThrThrThrAlaThrValLeuAlaGlnAlaIleIle |
| 301 | ACTGAAGGTCTGAAAGCTGTTGCTGCGGGCATGAACCCGATGGACCTGAAACGTGGTATC |
| 101 | ThrGluGlyLeuLysAlaValAlaAlaGlyMETAsnProMETAspLeuLysArgGlyIle |
| 361 | GACAAAGCTGTTACCGCTGCAGTTGAAGAACTGAAAGCGCTGTCCGTACCGTGCTCTGAC |
| 121 | AspLysAlaValThrAlaAlaValGluGluLeuLysAlaLeuSerValProCysSerAsp |
| 421 | TCTAAAGCGATTGCTCAGGTTGGTACTATCTCCGCTAACTCCGACGAAACCGTAGGTAAA |
| 141 | SerLysAlaIleAlaGlnValGlyThrIleSerAlaAsnSerAspGluThrValGlyLys |
| 481 | CTGATCGCTGAAGCGATGGACAAAGTCGGTAAAGAAGGCGTTATCACCGTTGAAGACGGT |
| 161 | LeuIleAlaGluAlaMETAspLysValGlyLysGluGlyValIleThrValGluAspGly |
| 541 | ACCGGTCTGCAGGACGAACTGGACGTGGTTGAAGGTATGCAGTTCGACCGTGGCATCCTG |
| 181 | ThrGlyLeuGlnAspGluLeuAspValValGluGlyMETGlnPheAspArgGlyIleLeu |
| 601 | TCTCCTATCTTCATCAACAAGCCGGAAACTGGCGCAGTAGAACTGGAAAGCCCGTTCATC |
| 201 | SerProIlePheIleAsnLysProGluThrGlyAlaValGluLeuGluSerProPheIle |
| 661 | CTGCTGGCTGACAAGAAAATCTCCAACATCCGCGAAATGATCCCGGTTATCGAAGCCGTT |
| 221 | LeuLeuAlaAspLysLysIleSerAsnIleArgGluMETIleProValIleGluAlaVal |
| 721 | GCCAAAGCAGGCAAACCGCTGCTGATCATCGCTGAAGATGTAGAAGGCGAAGCGTTCGCA |
| 241 | AlaLysAlaGlyLysProLeuLeuIleIleAlaGluAspValGluGlyGluAlaPheAla |
| 781 | ACTCTGCTTTTCAACACCATGCGTGGCATCGTGAAAGTTGCTGCAGTTAAAGCTCCGGGC |
| 261 | ThrLeuLeuPheAsnThrMETArgGlyIleValLysValAlaAlaValLysAlaProGly |
| 841 | TTCGGCGATCGTCGTAAAGCTATGCTGCAGGATATCGCAACCCTGACTGGCGGTACCGTA |
| 281 | PheGlyAspArgArgLysAlaMETLeuGlnAspIleAlaThrLeuThrGlyGlyThrVal |
| 901 | ATCTCTGAAGAGATCGGTATGGAGCTGGAAAAAGCAACCCTGGAAGACCTGGGTCAGGCT |
| 301 | IleSerGluGluIleGlyMETGluLeuGluLysAlaThrLeuGluAspLeuGlyGlnAla |
| 961 | AAACGCGTTGTGATCAACAAAGACACCACCACCATCATCGATGGCGTGGGCGAAGAAGCT |
| 321 | LysArgValValIleAsnLysAspThrThrThrIleIleAspGlyValGlyGluGluAla |
| 1021 | GCAATCCAGGGCCGTGTTGCTCAGATCCGTCAGCAGATTGAAGAAGCAACTTCTGACTAC |
| 341 | AlaIleGlnGlyArgValAlaGlnIleArgGlnGlnIleGluGluAlaThrSerAspTyr |

FIG. 4A

```
1081    GACCGTGAAAAACTGCAGGAGCGCGTAGCGAAACTGGCAGGCGGCGTTGCAGTTATCAAA
361     AspArgGluLysLeuGlnGluArgValAlaLysLeuAlaGlyGlyValAlaValIleLys

1141    GTAGGTGCTGCTACCGAAGTTGAAATGAAAGAGAAAAAAGCACGCGTTGAAGACGCCCTG
381     ValGlyAlaAlaThrGluValGluMETLysGluLysLysAlaArgValGluAspAlaLeu

1201    CACGCGACCCGTGCTGCGGTAGAAGAAGGCGTGGTTGCTGGTGGTGGTGTTGCGCTGATC
401     HisAlaThrArgAlaAlaValGluGluGlyValValAlaGlyGlyGlyValAlaLeuIle

1261    CGCGTAGCGTCTAAACTGGCTGACCTGCGTGGTCAGAACGAAGACCAGAACGTGGGTATC
421     ArgValAlaSerLysLeuAlaAspLeuArgGlyGlnAsnGluAspGlnAsnValGlyIle

1321    AAAGTTGCACTGCGTGCAATGGAAGCTCCGCTGCGTCAGATCGTCCTGAACTGCGGCGAA
441     LysValAlaLeuArgAlaMETGluAlaProLeuArgGlnIleValLeuAsnCysGlyGlu

1381    GAACCGTCTGTTGTTGCTAACACCGTTAAAGGCGGCGACGGCAACTACGGTTACAACGCA
461     GluProSerValValAlaAsnThrValLysGlyGlyAspGlyAsnTyrGlyTyrAsnAla

1441    GCAACCGAAGAATACGGCAACATGATCTGCATGGGTATCCTGGACCCAACCAAAGTAACC
481     AlaThrGluGluTyrGlyAsnMETIleCysMETGlyIleLeuAspProThrLysValThr

1501    CGTTCTGCTCTGCAGTACGCGGCTTCTGTGGCTGGCCTGATGATCACCACCGAATGCATG
501     ArgSerAlaLeuGlnTyrAlaAlaSerValAlaGlyLeuMETIleThrThrGluCysMET

1561    GTTACCGACCTGCCGAAAAACGATGCAGCTGACTTAGGCGCTGCTGGCGGCATGGGTGGC
521     ValThrAspLeuProLysAsnAspAlaAlaAspLeuGlyAlaAlaGlyGlyMETGlyGly

1621    ATGGGTGGCATGGGCGGCATGATGTAA
541     METGlyGlyMETGlyGlyMETMET***
```

FIG. 4B

PROTEIN SEPARATION DEVICE

CROSS REFERENCE TO RELATED APPLICATIONS

This application claims the benefit of U.S. Provisional Patent Application No. 60/530,608, which is incorporated herein by reference.

SEQUENCE LISTING

In accordance with 37 CFR §1.824, Applicant encloses herewith a copy of the Sequence Listing in computer readable form (CRF) on one compact disc, file name 51571-10 Seq 08-05-06 v1.txt, created May 8, 2006, file size 29 kilobytes, the contents thereof being incorporated by reference herein.

FIELD OF THE INVENTION

This invention relates to a device for the separation of proteins, in particular the separation of low molecular weight proteins from high molecular weight proteins, in a fluid sample, in particular a biological fluid sample; a method for using the device and to proteins obtainable by way of such a method.

BACKGROUND OF THE INVENTION

The study of the human proteome, in particular the human serum proteome, is an area of great interest, especially with respect to the pharmaceutical industry, with its potential to identify disease or biological markers. Studying this proteome presents a major challenge due to the varying concentrations of the constituent proteins of serum. These concentrations can vary by approximately ten orders of magnitude. Most of the pharmaceutically useful proteins are of the low molecular weight type and are found in low concentrations.

Human serum is typically comprised of blood with its constituent cells (erythrocytes and leucocytes) and clotting factors removed. The protein concentration of the serum is usually in the range of from 50 to 70 mg/ml. Approximately 70% of this protein is serum albumin (30 to 35 mg/ml) and 10% is IgG (5 to 7 mg/ml).

There are at least 10,000 proteins in human serum but most, approximately 95%, are at very low concentrations and have low molecular weights. For example, interleukin 6 (a marker for inflammation and/or infection) has a molecular weight of 21 kDa and is present in serum at a concentration of 10 pg/ml; a concentration of almost ten orders of magnitude less than serum albumin.

One of the most popular methods for examining the proteome is to use two-dimensional electrophoresis (2DE). Typically, this involves the separation of proteins by their isoelectric point and then by their molecular weight by SDS-PAGE.

2DE is advantageous as it has the potential to separate several thousand proteins as spots on one gel. The spots can then be excised from the gel, digested with trypsin and identified using MALDI-MS (matrix-assisted laser desorption ionisation mass spectroscopy). Other methods used in the separation of proteins include high-performance liquid chromatography and SELDI-MS (surface-enhanced laser desorption ionisation mass spectroscopy).

However, these methods usually involve a process of pre-fractionation and can result in the non-specific removal of proteins of interest that are associated with other proteins that are not of interest.

SUMMARY OF THE INVENTION

The present invention provides a protein separation device comprising a chaperone protein immobilised on a substrate.

In another aspect, the present invention provides a protein separation device comprising GroEL immobilised on a substrate in an optimised orientation to bind a target protein and to provide minimal steric hindrance between GroEL and the substrate.

In still a further aspect, the present invention provides a protein separation device comprising GroEL immobilised on a substrate, wherein the specificity of GroEL is directed to a particular protein.

In another aspect, the present invention provides a protein separation device comprising GroEL immobilised on a substrate, wherein the specificity of GroEL is changed to a specificity of another chaperone protein.

In yet another aspect, the present invention provides a protein separation device comprising GroEL in an optimised orientation to bind a target protein and to provide minimal steric hindrance between GroEL and the substrate wherein the specificity of GroEL is directed to a particular target protein.

The present invention also provides, in another aspect, a protein separation device comprising GroEL immobilised on a substrate in optimised orientation to bind a target protein and to provide minimal steric hindrance between GroEL and the substrate wherein the specificity of GroEL is changed to a specificity of another chaperone protein.

The present invention also provides, in a further aspect, a method of isolating at least one protein from a biological sample comprising the steps of:
a) denaturing a biological sample containing at least one protein;
b) applying the biological sample containing at the least one protein to a chaperone protein immobilised on a substrate.
c) isolating the at least one protein from the biological fluid on the chaperone protein;
d) removing the biological sample from the chaperone protein immobilised on the substrate, and
e) obtaining the at least one protein from the chaperone protein.

The present invention also provides, in another aspect, A method of identifying a biological marker in a biological sample comprising the steps of:
a) applying the biological sample containing the biological marker to a chaperone protein immobilised on a substrate;
b) isolating the biological marker from the biological fluid on the chaperone protein;
c) removing the biological sample from the chaperone protein, and
d) obtaining the at least one protein from the chaperone protein immobilised on the substrate.

The present invention also provides, in another aspect, a method of diagnosis comprising the steps of:
a) applying a biological sample from a first subject to a chaperone protein immobilised on a substrate;
b) isolating a protein from the biological fluid on the chaperone protein;
c) removing the biological sample from the chaperone protein;
d) obtaining the at least one protein from the chaperone protein, and
e) Comparing the concentration of the at least one protein from the first subject with a reference concentration obtained from a second subject.

BRIEF DESCRIPTION OF THE FIGURES

FIGS. 1a and 1b. Shows the peptide sequence and DNA codons of wild-type GroEL.

FIGS. 2a and 2b. Shows the peptide sequence and DNA codons of GroEL having Aspartate 490 substituted with Cysteine.

FIGS. 3a and 3b. Shows the peptide sequence and DNA codons of GroEL with the mutations Leucine 200→Arginine, Serine201→Tyrosine, Proline202→Aspartate and Aspatate490→Cysteine.

FIGS. 4a and 4b. Shows the peptide sequence and DNA codons of GroEL with the mutations Tyrosine199→Isoleucine, Tyrosine204→Isoleucine, Leucine234→Isoleucine, Leucine237→Isoleucine, Leucine259→Phenyalanine, Valine263→Leucine and Valine264→Phenylalanine and Aspartate490→Cysteine.

DETAILED DESCRIPTION OF THE INVENTION

Materials

Figure 5:
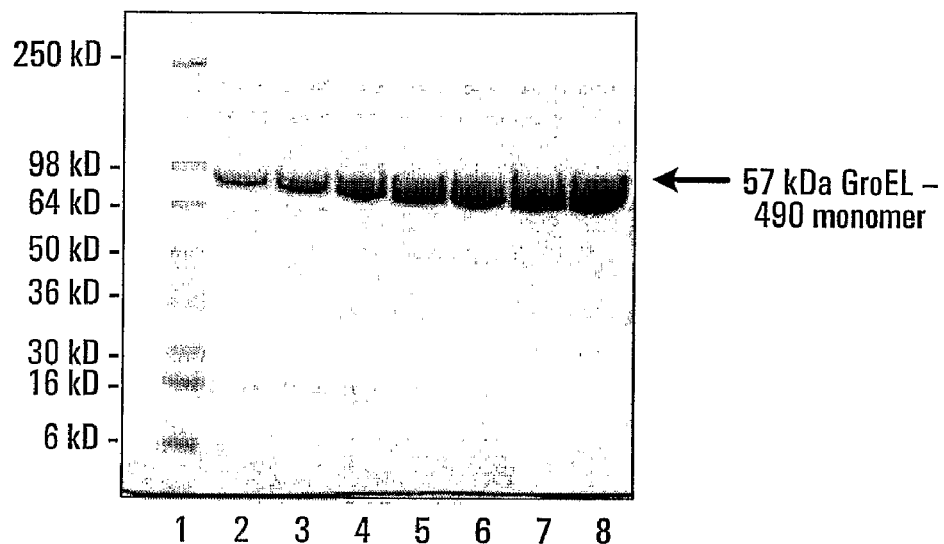
FIG. 5. Shows a polyacrylamide gel of GroEL monomers of ~57 kDa from eluted fractions of a column.

A biological sample may be obtained from a human subject. The sample is preferably a fluid but may also be some other biological extract. It will be appreciated that the application of the invention is not to be limited to humans but can be used on a biological sample from any animal. The fluid may comprise, but is not limited thereto, serum, cerebrospinal fluid, urine, nipple aspirant, other biological fluids, extracts, tissue extracts or other mixture of proteins.

Chaperone Proteins

Chaperone proteins bind to non-native (denatured) states of other proteins and assist them to reach a functional conformation. This is achieved in most cases through the expenditure of ATP. Originally identified by their increased abundance following heat shock, chaperone proteins in general recognise exposed hydrophobic surfaces of non-native species of proteins and form non-covalent interactions with them, stabilising them against irreversible multimeric aggregation. Release of the polypeptide then follows, in many cases driven by an ATP-directed conformational change in the chaperone protein, permitting subsequent steps of polypeptide folding to occur. When such steps fail to proceed to a native conformation, recognition and rebinding by the same or other chaperone protein can occur, allowing another opportunity for a productive conformation to be reached.

Different classes of chaperones are directed to binding specific non-native states. For example, Hsp70 and Hsp60 (chaperoning chaperones recognise, respectively, extended and collapsed conformations, which are bound correspondingly either by local enclosure of the polypeptide chain or by global enclosure of the polypeptide in a central enclosure.

The present invention takes advantage of the chaperone's ability to recognise a non-native state of a protein to separate that protein from other proteins present in a biological sample. Advantageously, chaperones are also able to select non-native proteins by their molecular weight. This feature of chaperones is also exploited to isolate low molecular weight proteins from a biological sample.

Advantageously the present invention will work with any chaperone protein.

The chaperone is preferably selected from the group consisting of Hsp100, Hsp90, Hsp70, Hsp60 and small Hsps, for example Hsp25 and the like. Preferably, the chaperone may be an Hsp60 chaperone of the group I chaperonin type. More preferably, the chaperone may be of the chaperonin type possessing peptide-dependent ATPase activity. Most preferably, the chaperonin may be, for example, GroEL.

Preferably, GroEL may be in operative association with a co-factor. The co-factor may be, for example, the co-chaperonin, GroES or a fragment thereof.

Although the mechanism of GroEL in protein folding is well documented in the art, it will be appreciated, by those of skill in the relevant art, that the following proposed mechanism is a theory and the invention should not be construed as being limited to any particular theory in the art or that proposed herein.

GroEL (also referred to as Hsp60) is of the group I chaperonin type. The term chaperonin refers to the double ring structure that these proteins generally comprise. Typically, these proteins present as heptameric, double-ring assemblies that promote the folding of proteins from a non-native or denatured state to the native state. The structure of GroEL is arranged in a back-to-back fashion of identical or closely related rotationally symmetrical subunits.

The rings of GroEL define a central, generally cylindrical, cavity that functions in two conditions. In a first operative condition, GroEL is open at an end of the cylindrical cavity to allow ingress of non-native proteins. The opening is provided with a flexible hydrophobic lining located in an apical domain of each subunit in the ring structure. The hydrophobic lining binds to non-native proteins in a multivalent interaction between their respective exposed hydrophobic surfaces.

In a second operative condition the binding of ATP, to an equatorial domain of GroEL, together with a co-chaperonin, GroES, at a location in an apical domain of GroEL per se induces a conformational change in the ring structure.

GroES is advantageous as it limits the size of proteins captured by GroEL to ~57 kDa or less.

The conformational change preferably comprises the en bloc movement of the seven apical domains of each of the subunits in the ring structure resulting in a global change to the internal milieu of the central cylindrical cavity. The cavity increases in volume by almost two-fold and is closed off by GroES. The hydrophobic surface at the apical domain is then elevated and twisted away from the non-native polypeptide causing the peptide to be released into the central cavity. The cavity is now predominantly hydrophilic in character, favouring the burial of exposed hydrophobic amino acid residues and the promotion of the native state of the polypeptide.

The non-native protein may undergo many rounds of capture and release by GroEL until the polypeptide has refolded into its native state. The capture and release may be performed by the same GroEL protein or by different a GroEL protein.

Preferably, GroEL is used in its wild-type double ring structure of a chaperonin. Alternatively, GroEL may be utilised in a single, heptameric, ring form.

One ring of GroEL may comprise a heptameric ring and the other ring may comprise a dimeric, trimeric, tetrameric, pentameric or a hexameric structure.

GroEL may also, for example, comprise a heptameric ring of wild-type GroEL and a ring of another chaperonin protein, for example, rubisco subunit binding protein or CCT.

GroEL may further comprise a double ring assembly wherein one or both rings comprise one or more subunits from other chaperonins and each ring may be a heteromeric heptamer.

For example the rings may contain one or more of each of the α, β, γ, δ, ε, ζ or θ subunits of CCT (TCP-1) or one or more subunits of rubisco subunit binding protein. Alternatively, GroEL may comprise a double ring assembly wherein the or each ring comprises one or more subunits from other chaperoning.

GroEL used in the present invention may take any of the forms listed above, including fragments of chaperone proteins, and any combination thereof.

The chaperonin GroEL may be obtained from a microbial source selected from the group consisting of bacteria and archaea, for example, those of *Escherichia* spp., *Thermus* spp. *Streptococcus* spp., *Staphylococcus* spp., *Bacillus* spp., *Leptospira* spp., *Spirillum* spp., *Lactobacillus* spp., *Mycoplasma* spp., *Pseudomonas* spp., *Streptomyces* spp., *Corynebacterium* spp., *Bacteroides* spp. and *Clostridium* spp. GroEL is preferably isolated from *Escherichia coli*. Alternatively GroEL may be isolated from *Thermus thermophilus* or *Clostridium difficile*.

Substrate

The substrate is preferably a solid support of the array or bead type. These may be manufactured from any suitable material known to those of skill in the art, for example a plastics material. Typically, supports of the array type may be provided with a variety of surfaces, located in spots on the substrate, to permit the protein of the chaperone type to be immobilised thereon. These surfaces may be comprised of moieties selected from the group consisting of, inter alia, nitriloacetic acid, carboxylates, quaternary amines, silicates, carbonyl diimidazoles and epoxides. The substrate may be provided with an hydrophobic barrier coating.

Suitable substrates for use in the present invention are, for example, bio-chips available from Ciphergen® or NeutrAvidin beads available from Pierce.

Modification of the Chaperone Protein

The chaperone protein of the present invention may be modified in order to alter its properties. For example, the chaperone may be modified to improve its binding to a target protein or improve folding functions. Typically such modifications are achieved by deleting, introducing or mutating specific codons in the DNA/cDNA sequence of the chaperone. Typically this may be carried out using site-directed mutagenesis. Site-directed mutagenesis may be performed by polymerase chain reaction or some other suitable method known to those of skill in the art.

It will be appreciated that modifications made to the amino acid sequence of GroEL may be of the conservative type, for example, substitution of polar-to-polar, non-polar to non-polar or aromatic-to-aromatic residues. Alternatively non-conservative substitutions may be made to the amino acid sequence of GroEL. For example, polar to non-polar residue substitutions.

The modified amino acid sequence of GroEL may be 70-80% homologous to SEQ ID No. 2. The sequence may be 90-95% homologous to SEQ ID No. 2. Alternatively, the amino acid sequence may be 96, 97, 98 or 99% homologous to SEQ ID No. 2.

Homology/Hybridization

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

As defined herein, the expression "GroEL" includes variants of native GroEL polypeptide, for example: deletions, including truncations and fragments; insertions and additions, including tagged polypeptides and fusion proteins; substitutions, for example site-directed mutants and allelic variants.

As used herein, "polypeptide" means any chain of amino acids, regardless of length or post-translational modification (e.g., glycosylation or phosphorylation), and include: natural proteins; synthetic or recombinant polypeptides and peptides as well as hybrid molecules (e.g. a fusion protein or chimera having one portion comprising all or part of a polypeptide of the invention and a second portion comprising an amino acid sequence from another protein or peptide); modified peptides, including for example peptoids having one or more non-amino acyl groups (q.v., sugar, lipid, etc.) covalently linked to the peptide; and peptidomimetics. Typically the protein or polypeptide may be isolated or substantially pure or recombinant.

The modifications may include, without limitation, the introduction of a proteolytic cleavage site; an N- or O-linked glycosylation site in which the N-linked glycosylation site is a high mannose type, a hybrid type or a complex type glycosylation site; an acylation site, for example, a myristoylation site; a methylation site; a phosphorylation site; a sulphation site and a prenylation site, for example, a farnesyl or geranyl site.

Preferably, modification of the chaperone protein may be performed to:
a) optimise the orientation of the immobilised chaperone and minimise steric hindrance between the chaperone and a solid substrate;
b) direct the target specificity of the chaperone, and
c) alter the target specificity of the chaperone.

In order to optimise the orientation of the GroEL chaperonin and minimise steric hindrance, Asp490 may be substituted with a Cys residue (SEQ ID No. 2). This mutation introduces a thiol group in the equatorial domain of GroEL. The thiol group may, for example facilitate the introduction of biotin at this site. This is advantageous as immobilisation of GroEL on an array or a bead can be achieved by taking advantage of the interaction between biotin located in GroEL and a streptavidin moiety located on an array or a bead.

To direct the target specificity of the GroEL chaperonin, the mutations Leu200→Arg, Ser201→Gly and Pro202→Asp (SEQ ID No. 3) introduce, into the apical domain of the subunits of GroEL, a consensus binding motif, RGD, specific for the integrin family of proteins. Integrins are important in cell-to-cell and cell-matrix interactions; and have been implicated in cell signalling. The above mutations may also comprise, for example, the binding motifs RCD and RYD, which are also recognised by integrins. This is advantageous as modification of GroEL in the apical domain allows the target specificity to be directed towards a specific group or family of proteins.

It will be appreciated that any binding motif could be introduced into a binding domain of any chaperone used in the present invention in order to isolate a specific protein or family of proteins.

To alter the target specificity of GroEL, the mutations Tyr199→Ile, Tyr204→Ile, Leu234→Ile, Leu237→Ile, Leu259→Phe, Val263→Leu and Val264→Phe (SEQ ID No. 4) may be made in the apical protein-binding domain of GroEL. These mutations result in the replacement of the substrate binding specificity of GroEL, a group I chaperonin, with that of Thermosome, a group II chaperonin. This is advantageous as it allows the capture by the modified GroEL of targets that were previously unavailable to wild-type GroEL. Alternatively, other mutations may be made to replace the substrate binding specificity of GroEL with CCT or rubisco subunit binding protein.

This is advantageous as it allows for the possibility of increased capture of proteins by various forms of GroEL on an array or a bead. The array or bead may comprise one or more different types of mutated GroEL. Alternatively, for example, a first array or a bead may comprise only wild-type of GroEL and may be assayed with a biological sample in parallel with a second array or bead comprising a further type of mutated GroEL.

Preparation of the Protein Separation Device

The protein separation device in accordance with the present invention may conveniently take the form of an array or a bead or other suitable solid support known to those skilled in the art.

The array or bead is preferably prepared in accordance with the manufacturer's instructions. Typically, for an array this involves the steps of:
a) rehydrating one or more spots located on the array in the recommended buffer;
b) loading the one or more spots with a chaperone, and
c) Incubating the array overnight in an humidifier.

Preferably, 1 to 10 µg/ml of GroEL may be loaded on to the or each spot. More preferably 2 to 8 µg/ml, more preferably 4 to 8 µg/ml, more preferably 5 to 7 µg/ml and most preferably 6 µg/ml of GroEL may be loaded onto the or each spot.

The array may be incubated in an humidifier at 4° C. overnight.

Preferably, from 0.25 to 3 pmole of protein is immobilised on the or each spot. More preferably 0.5 to 2 pmole, more preferably 0.5 to 1.5 pmole and most preferably 1 pmole of protein is immobilised on the or each spot on the array.

Biological Sample Denaturation

The protein in a biological sample for use in the present invention may be denatured using reagents selected from the group consisting of chaotropic agents, detergents, heat, reducing agents, oxidising agents, laser-induced denaturation and sonication.

Preferably, the chaotropic agent may be selected from guanidine hydrochloride, guanidine thiocyanate, urea, thiourea, sodium thiocyanate and ammonium sulphate Preferably the detergent may be, for example, sodium dodecyl sulphate.

Preferably, the reducing agent may be selected from dithiothreitol (Cleland's reagent), dithioerythritol and 2-mercaptoethanol.

Preferably, the oxidising agent may be hydrogen peroxide.

The biological sample may be denatured by a combination of the above-mentioned denaturing agents. Most preferably the biological sample is denatured by, for example, a buffer comprising a chelating agent, for example, EDTA; dithiotreitol and guanidine hydrochloride.

The biological sample is denatured for about 1 to 2 hours in the denaturation buffer. The biological sample may be subsequently diluted in binding buffer. This step allows the denatured protein to partially renature and promote the binding of the protein to GroEL. At high salt concentrations, for example, above 5M guanidine HCl, the chaotropic effect of the salt is too great for GroEL to bind to the denatured protein.

Isolation of Denatured Proteins in a Biological Sample

Figure 10:
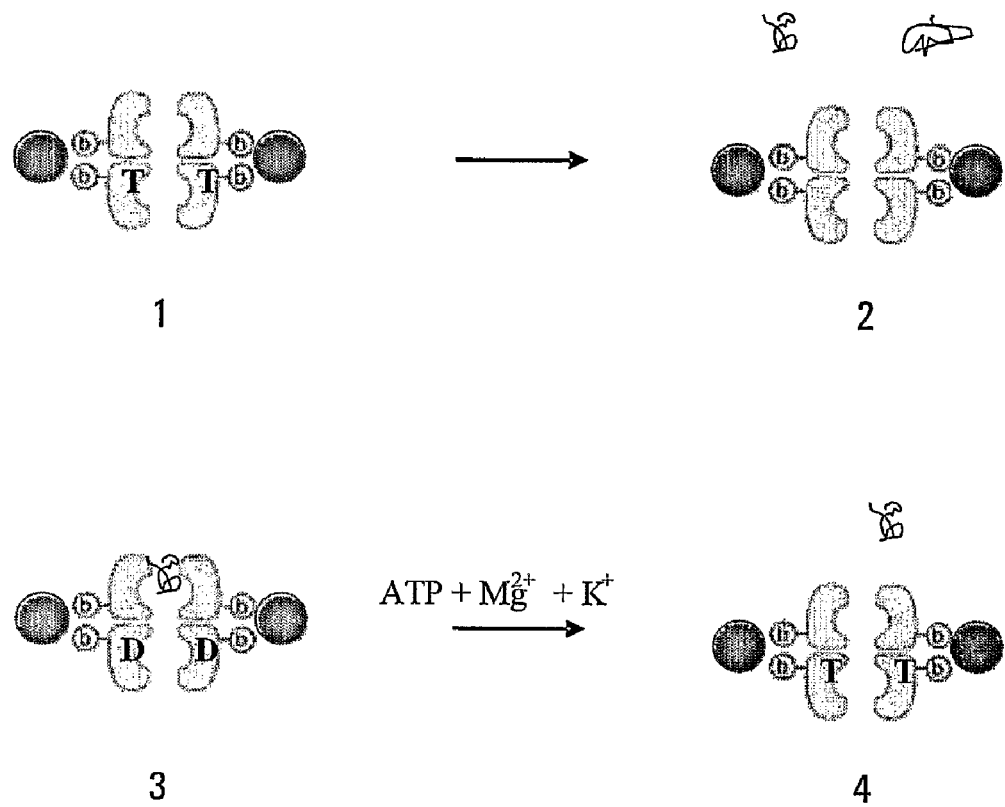
FIG. 10. is an illustration of the mechanism of GroEL when immobilised on NeutrAvidin beads.

Referring to FIG. 10, the mechanism of protein separation by GroEL is illustrated. GroEL is shown conjugated onto a NeutrAvidin bead. The beads would typically be located in a column. The GroEL may first be primed with ATP (T=ATP). The denatured substrate from the biological sample may be introduced into the column, after being partially renatured, for binding to GroEL. The renatured substrate may interact with the cis cavity of GroEL. The protein may then be encapsulated. In the absence of GroES, GroEL can partially encapsulate proteins to 82 kDa or greater (Chaudhuri et al., 2001). After washing to remove proteins that have bound non-specifically, the captured protein(s) are released by the addition ATE in the presence of co-factors $Mg^{2+}$ and $K^+$. When protein separation is carried out in the presence of GroES the protein is limited to ~57 kD and below.

The protein separation device according to the invention may be incubated with a biological sample containing denatured proteins. The biological sample is preferably suspended in a physiological buffer. The biological sample may be incubated with the protein separation device for between 1 to 5 hours and most preferably for about 4 hours at ambient room temperature. Alternatively, the incubation period is from 10 to 20 minutes.

Any non-specific binding can be removed by washing the protein separation device in a suitable buffer. The captured proteins of interest may be released by ATP in the presence of $Mg^{2+}$ and $K^+$.

The protein separation device may be processed using, for example, using a suitable output device available from, for example, Ciphergen®.

Uses

The protein separation device in accordance with the present invention may be useful in the identification of biological markers for disease. For example, the protein separation device may isolate proteins from a patient suffering from a particular disease that are only expressed in the diseased state when referenced with a normal subject. Alternatively, these isolated proteins may be under-expressed or over-expressed in the diseased state.

The protein separation device may be useful to test the protein composition of a biological sample, with particular reference to biological markers, prior to and subsequent of an administration of a pharmaceutical or neutraceutical compound. The results could give an indication, for example, of the side effects of a particular compound. This may find application in the screening of pharmaceutical or neutraceutical compounds.

The protein separation device may also be useful in the prognosis of a disease state. The protein separation device may be used to screen for biological markers in a biological sample prior, during and after treatment of a disease state to assess the efficacy of a particular treatment regime or protocol.

The protein separation device may further be used to diagnose a disease by assaying for changes in the relative concentrations of important biological markers in a biological sample.

Advantageously, the present invention may find particular application in the diagnosis of disease associated with proteins that have not folded correctly, for example those diseases selected from cystic fibrosis, Alzheimer's disease, emphysema, Huntington's disease, spinocerebellar ataxia type 3, primary lateral sclerosis and amyotrophic lateral sclerosis. Most preferably the present invention may be used in the diagnosis of transmissible spongiform encephalopathies, for example, Creutzfeld-Jakob Disease, variant Creutzfeld-Jakob Disease, Gerstmann-Straussler-Scheinker Syndrome, Fatal Familial Insomnia, Kuru, Atypical Prion Disease, Bovine Spongiform Encephalopathy, Scrapie, Feline Spongiform Encephalopathy, Transmissible Mink Encephalopathy, Chronic Wasting Disease, Exotic Ungulate Encephalopathy.

The protein separation device may further be used to isolate proteins from any denatured biological sample.

The following example is offered by way of illustration and not by way of limitation.

Example 1

This example describes the purification of a modified GroEL protein.

Cell Culture

Approximately 6 litres of an *E. coli* bacterial cell culture transformed with an expression plasmid comprising GroEL was incubated in Luria broth (Invitrogen) in a shaker (250 rpm) at 37° C. When the optical density of the culture reached 0.6, 1 mM of IPTG (isopropyl-d-thiogalactopyranoside) was added to the culture. The culture was then incubated for a further 4-5 hours. Bacterial cells were subsequently harvested by centrifugation at 4000×g for 10 minutes and the cell pellets were stored at −80° C.

Purification of GroEL

A frozen cell pellet was resuspended in 45 ml of buffer A [50 mM Tris-HCL pH 7.5, 1 mM DTT, 0.1 mM PMSF (phenylmethylsulfonyl fluoride) and 1 mM EDTA]. The cell suspension was passed through a French press three times with an internal cell pressure of 1,000 psi to obtain a cell lysate. The cell lysate was centrifuged at 20,000×g for 0.5 hour. The supernatant was isolated and supplemented with 20% ammonia sulphate. The supernatant was then injected into a butyl-toyopearl hydrophobic interaction column (Tosoh Corporation, Japan). The column was pre-equilibrated with 23% ammonia sulphate and 20% methanol in buffer A. The injected sample was allowed to reach equilibrium for 15 minutes. The column was then washed with the buffer A.

Subsequently, GroEL was eluted by means of a reverse linear gradient of ammonia sulphate, i.e. a gradient of 23% to 0%, in buffer A.

Eluted fractions containing GroEL were pooled and GroEL was reconstituted into its double heptameric ring configuration by precipitating the pooled fractions in 70% Ammonia sulphate supplemented with 5 mM $MgCl_2$ and 3 mM ATP. The precipitate was pelleted at 20,000×g and resuspended in buffer A containing 10% glycerol and stored at −80° C.

Figure 6:
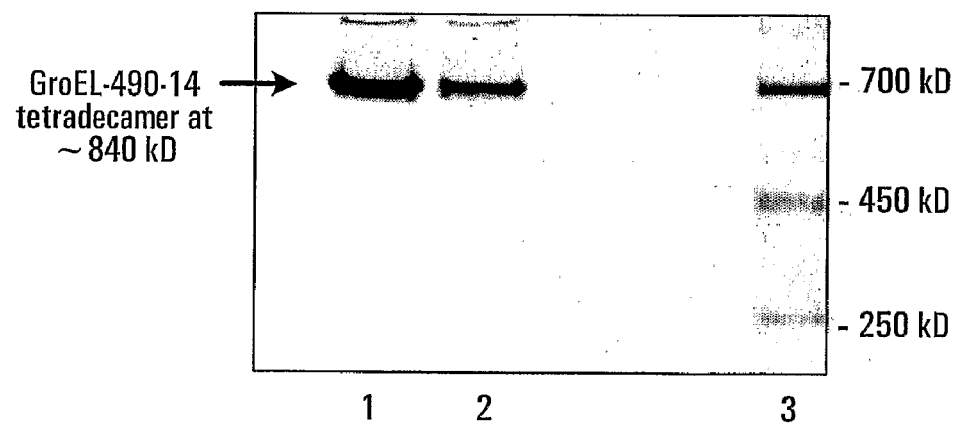
FIG. 6. Shows a polyacrylamide gel of GroEL in a wild-type double heptamer ring configuration of ~840 kDa from eluted fractions of a column.

Typically 6 liters of cell culture will yield approximately 250 mg of >95% pure GroEL, see FIGS. 5 and 6. FIG. 5 shows a coomassie-stained SDS-PAGE gel of fractions from a butyl-toyopearl hydrophobic interaction column. GroEL was purified to ~>95% purity. Lane 1=Molecular weight marker (See-Blue Pre-stained Standard, from Invitrogen Catalog code: LC5625) lanes 2-8 are, respectively, 2, 4, 6, 8, 10, 14, 16 μg of total loaded protein. FIG. 6 shows a coomassie-stained native PAGE gel showing the purity of reconstituted GroEL-490-14. Lanes 1 and 2 represent 10 and 5 μg of native GroEL-490 respectively. Lane 3 is a molecular weight marker (High molecular weight markers for native electrophoresis from Amersham biosciences, product code: 17-0445-01).

GroEL-490 was then conjugated onto NeutrAvidin beads and tested for ATPase activity and protein folding properties. The reconstituted GroEL was to function as an ATPase and to be capable of protein folding, see FIG. 7 and FIG. 8.

Figure 7:
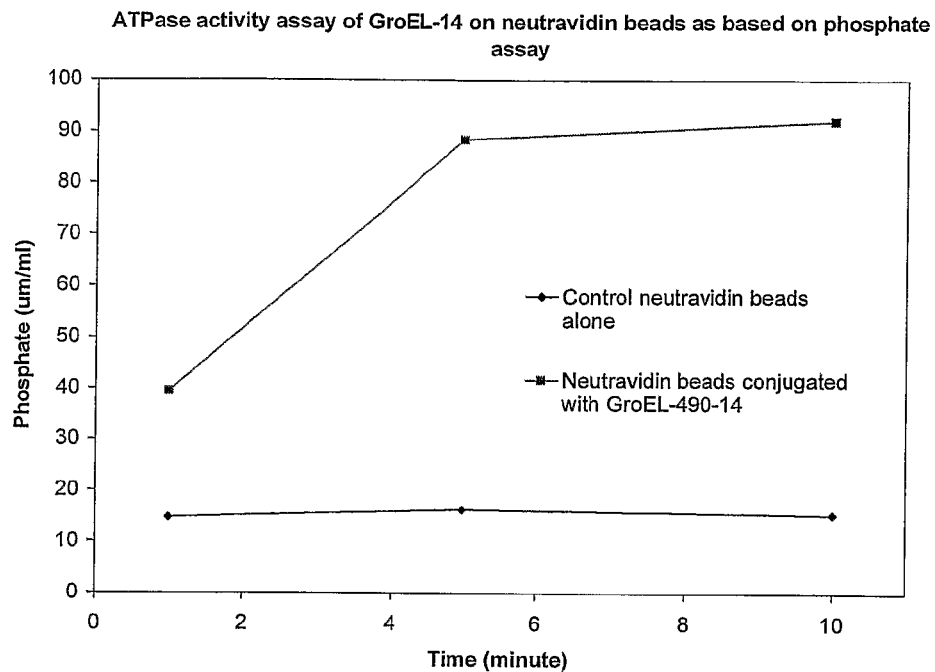
FIG. 7. Shows the results of an ATPase assay of biotinylated GroEL immobilised on NeutrAvidin beads.
Figure 8:
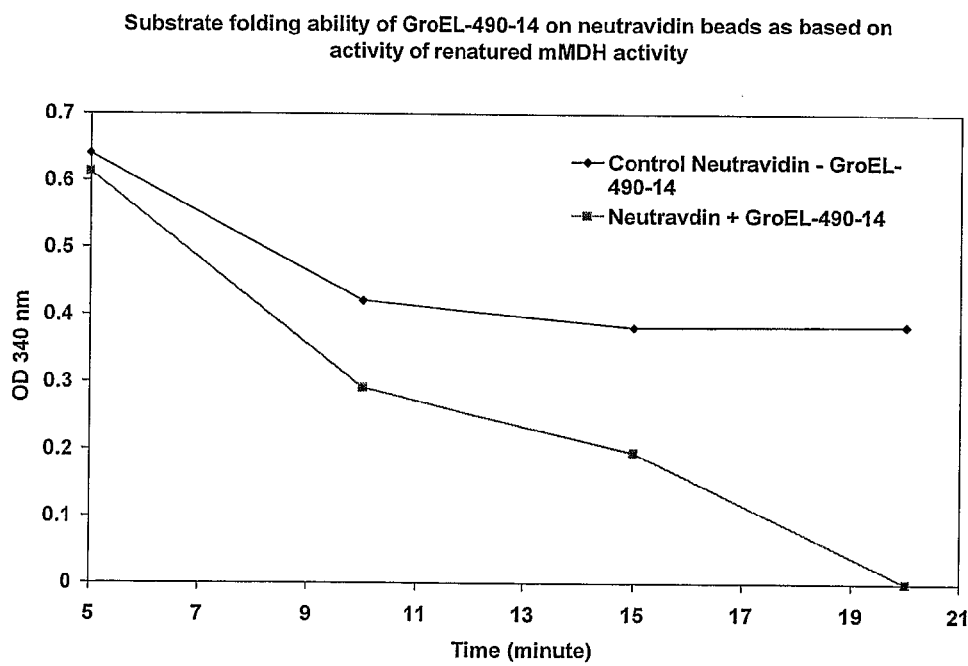
FIG. 8. Shows the results of a protein folding assay by biotinylated GroEL immobilised on NeutrAvidin beads.
Figure 9:
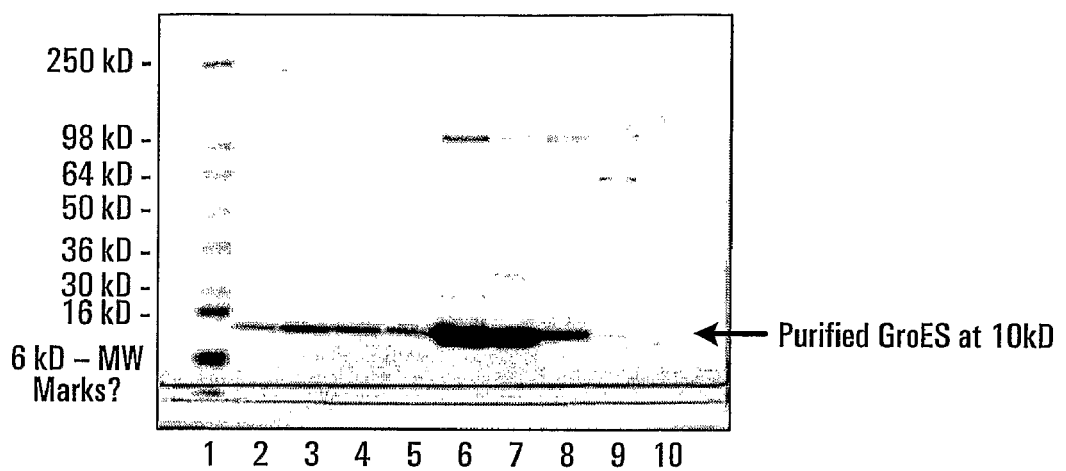
FIG. 9. Shows a polyacrylamide gel of purified GroES in eluted fractions from a column.

FIG. 7 demonstrates the ATPase activity of GroEL490 on NeutrAvidin beads using an Enzchek phosphate assay kit from molecular Probes (Catalog code: E-6646). Each data point is the average of two separate experiments and ~2 mg of GroEL-490 was used for the activity assay. FIG. 8 shows the substrate folding ability of GroEL-490 on NeutrAvidin beads.

The substrate folding ability was tested by the ability to refold denatured mitochondrial malate dehydrogenase (mMDH). The assay protocol was taken from Staniforth et al., 1994. Each data point is the repeat of two separate experiments. Briefly, native mMDH will have the ability to convert NADH (OD at 340 nm) to $NAD^+$ (no OD at 340 nm) in the presence of oxaloacetate. Therefore, positive GroEL-490 activity was confirmed by a reduction in OD at 340 nm with respect to the control.

Purification of GroES

GroES was purified using a DEAE anion exchange column (Biorad). *E. coli* transformed with GroES expression plasmids were grown in a similar way as *E. coli* transformed with GroEL expression plasmids. However, the cell lysate obtained after French pressing was incubated at 80° C. for 20 minutes to coagulate heat sensitive proteins present in the lysate. The coagulated proteins were then centrifuged at 12,000×g for 20 minutes. The supernatant was decanted and injected into DEAE column equilibrated with buffer A. The supernatent was allowed to equilibrate with the column for 20 minutes. The column was then washed with buffer A and GroES was eluted using a linear gradient of 0 to 0.6 M NaCl in buffer A.

Eluted fractions containing GroES were identified by SDS-PAGE, pooled and reconstituted into its heptameric configuration in 70% ammonia sulphate in the absence of $MgCl_2$ and ATP. Typically, 6 liters of bacterial cell culture will give approximately 150 mg of >95% pure GroES, see FIG. 5.

FIG. 5 shows a coomassie-stained gel of GroES containing fractions eluted from a column. These fractions were confirmed by SDS-PAGE to be >95% pure. Lane 1=molecular weight markers, lanes 2-10 are consecutive fractions from a column (5 ml each).

Example 2

This example describes the isolation of proteins from a biological sample using the protein separation device in accordance with the present invention.

Serum was derived from a human blood sample. The Protein separation device comprised GroEL immobilised on a bio-chip array such as those available from Ciphergen® or GroEL conjugated to beads, for example NeutrAvidin beads, available from Pierce. All other reagents were obtained from Sigma.

The protein separation device was prepared as follows:

Approximately 75 mg-100 mg of GroEL490 was passed through a PD10 (Amersham) desalting column in PBS-EDTA (5 mM) buffer. Desalted GroEL490 was biotinylated in PBS-EDTA buffer containing biotin-HPDP based on manufacturer's guidelines for recommended usage. The biotinylation reaction proceeded to completion in ~2 hours. This was confirmed using a spectrometer at an absorbance of 343 nM.

Excess biotin was removed by using a PD10 desalting column. Biotinylated GroEL-490 was then conjugated onto NeutrAvidin beads by incubating the protein with the beads for 1 hour in PBS buffer (pH 7.5). 10 ml of the NeutrAvidin medium is sufficient to conjugate ~75-100 mg of GroEL-490.

Beads conjugated with GroEL-490 were then packed into a column. The beads were washed with 5 column volumes of buffer W (50 mM Tris-HC, pH 7.5, 100 mM KCL, 5 mM $MgCl_2$, 0.1 mM DTT, 0.3 mM EDTA). Following this washing step, the column was washed with 2 column volumes of buffer W supplemented with 3 mM ATP to remove any bound endogenous proteins from *E. coli*. The column was then washed with 8 column volumes of buffer W. The column was then ready for use.

75 μl of human serum was denatured using 25 μl of denaturation buffer (6M guanidine-HCl, 2 mM EDTA and 10 mM dithiothreitol) at ambient room temperature for 1 hour.

The serum was then diluted 30-50 fold in binding buffer (50 mM Tris-HCl, pH 7.4; 10 mM $MgCl_2$; 10 mM KCl) and immediately loaded on to the column. The serum was left on the column for 20 minutes. The column was then washed with 10 column volumes of buffer W.

At the end of this wash step proteins bound to GroEL-490, regardless of their state of folding, eluted from the column with 3 column volumes of buffer W supplemented with 3 mM ATP. Eluted fractions were collected and protein peaks were determined by BCA assay (invitrogen). Eluted fractions of interest were pooled and proteins were concentrated for identification using Liquid Chromatography Mass Spectroscopy.

The data obtained showed that by means of comparison as based on LC-MS-MS results, the protein separation device of the present invention can generate more information (more than seven-fold) from a biological sample (see Table 1) with respect to a conventional method of enriching low molecular weight proteins, for example, gel filtration (See Table 2). Also the distribution of capture protein species is more even than those by gel filtration (Table 1 and Table 2).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

TABLE 1

| | Normal serum GroEL capture | | | | | |
|---|---|---|---|---|---|---|
| DTASelect v1.9 Locus Unique | Sequence Count FileName | Spectrum Count XCorr | Sequence Coverage DeltCN | MolWt CalcM + H+ | pI Total Intensity | Descriptive Name SpScore IonProportion Redundancy Sequence |
| gi\|4502027\|ref\|NP__000 | 89 | 475 | 77.20% | 69367 | 6.3 | albumin precursor; PRO0883 protein [*Homo sapiens*] |
| gi\|10442822\|ref\|NP__05 | 3 | 113 | 1.40% | 527615 | 6 | baculoviral IAP repeat-containing 6 [*Homo sapiens*] |
| gi\|42659147\|ref\|XP__37 | 3 | 110 | 11.80% | 50328 | 5.7 | similar to CXYorf1-related protein [*Homo sapiens*] |
| gi\|4557871\|ref\|NP__001 | 36 | 60 | 47.70% | 77050 | 7.1 | transferrin; PRO2086 protein [*Homo sapiens*] |
| gi\|20143922\|ref\|NP__59 | 48 | 56 | 3.80% | 3013989 | 6.7 | titin isoform novex-2; connectin; CMH9, included; cardiomyopathy, dilated 1G (autosomal dominant) [*Homo sapiens*] |
| gi\|20143967\|ref\|NP__61 | 1 | 53 | 1.60% | 110059 | 8.5 | kinesin family member 23 isoform 1; mitotic kinesin-like 1; kinesin-like 5 (mitotic kinesin-like protein 1) [*Homo sapiens*] |
| gi\|4557225\|ref\|NP__000 | 31 | 43 | 28.10% | 163277 | 6.4 | alpha 2 macroglobulin precursor [*Homo sapiens*] |
| gi\|4557385\|ref\|NP__000 | 28 | 43 | 24.80% | 187163 | 6.4 | complement component 3 precursor; acylation-stimulating protein cleavage product [*Homo sapiens*] |
| gi\|4504253\|ref\|NP__002 | 3 | 41 | 23.10% | 15145 | 10.7 | H2A histone family, member X; H2AX histone [*Homo sapiens*] |
| gi\|9966821\|ref\|NP__065 | 2 | 41 | 6.60% | 68960 | 7.6 | ectonucleoside triphosphate diphosphohydrolase 7; lysosomal apyrase-like protein 1 [*Homo sapiens*] |
| gi\|4505723\|ref\|NP__002 | 2 | 38 | 6.50% | 44130 | 8.1 | peroxisome biogenesis factor 13 [*Homo sapiens*] |
| gi\|11321561\|ref\|NP__00 | 19 | 35 | 37.20% | 51676 | 7 | hemopexin [*Homo sapiens*] |
| gi\|34485727\|ref\|NP__00 | 2 | 35 | 1.20% | 128153 | 6.9 | hematopoletic protein 1; membrane-associated protein hem-1 [*Homo sapiens*] |
| gi\|21351612\|ref\|NP__07 | 2 | 34 | 4.30% | 61949 | 8 | HpaII tiny fragments locus 9C isoform2 [*Homo sapiens*] |
| gi\|12083581\|ref\|NP__05 | 4 | 34 | 8.10% | 138567 | 6.2 | phosphoinositide-specific phospholipase C beta 1 isoform a; 1-phosphatidylinositol-4,5-bisphosphate phosphodiesterase beta 1; PLC-beta-1; triphosphoinositide phosphodiest |
| gi\|37540833\|ref\|XP__03 | 3 | 33 | 1.30% | 341363 | 7.1 | MAX dimerization protein 5 [*Homo sapiens*] |
| gi\|18254460\|ref\|NP__54 | 1 | 30 | 14.30% | 30179 | 9.3 | SPRY domain-containing SOCS box protein SSB-4 [*Homo sapiens*] |
| gi\|4885637\|ref\|NP__005 | 3 | 30 | 14.40% | 53818 | 4.7 | target of myb1; target of myb 1; target of myb1 (chicken) homolog [*Homo sapiens*] |
| gi\|14149734\|ref\|NP__06 | 3 | 28 | 12.70% | 54235 | 5.9 | coronin, actin binding protein, 1B [*Homo sapiens*] |
| gi\|42661355\|ref\|XP__29 | 4 | 28 | 4.20% | 75410 | 5.8 | similar to KIAA1074 protein [*Homo sapiens*] |
| gi\|21361452\|ref\|NP__05 | 4 | 27 | 10.90% | 73427 | 7.8 | glutaminase C; L-glutamine amidohydrolase; K-glutaminase; glutaminase, phosphate-activated [*Homo sapiens*] |
| gi\|4507825\|ref\|NP__001 | 1 | 26 | 4.20% | 60695 | 8.3 | UDP glycosyltransferase 2 family, polypeptide B7; UDP-glucuronyltransferase, family 2, beta-7 [*Homo sapiens*] |
| gi\|40805845\|ref\|NP__00 | 5 | 24 | 3.90% | 305244 | 7.8 | DNA polymerase theta isoform 1; polymerase (DNA-directed), theta [*Homo sapiens*] |
| gi\|20149635\|ref\|NP__05 | 2 | 22 | 7.80% | 40573 | 5.1 | p47 protein isoform a [*Homo sapiens*] |
| gi\|42718017\|ref\|NP__97 | 2 | 22 | 2.50% | 98434 | 6.6 | retinoblastoma binding protein 8 isoform b; CTBP-interacting protein; retinoblastoma-interacting myosin-like [*Homo sapiens*] |
| gi\|27659724\|ref\|NP__00 | 2 | 21 | 12.10% | 25173 | 8.5 | synovial sarcoma, X breakpoint 2 isoform a; sarcoma, synovial, X-chromosome-related 2; SSX2 protein [*Homo sapiens*] |
| gi\|15208665\|ref\|NP__15 | 2 | 21 | 10.40% | 49773 | 7.9 | tripartite motif protein TRIM14 isoform alpha; tripartite motif protein TRIM14; tripartite motif protein 14 [*Homo sapiens*] |
| gi\|21361198\|ref\|NP__00 | 10 | 20 | 23.20% | 46723 | 5.6 | serine (or cysteine) proteinase inhibitor, clade A (alpha-1 antiproteinase, antitrypsin), member 1; Protease inhibitor (alpha-1-antitrypsin); protease inhibitor 1 (anti-e |
| gi\|41151008\|ref\|XP__09 | 3 | 19 | 6.40% | 79360 | 9.2 | similar to BC331191_1 [*Homo sapiens*] |
| gi\|41203848\|ref\|XP__37 | 6 | 19 | 12.00% | 84926 | 4.8 | similar to Ig alpha-2 chain C region [*Homo sapiens*] |
| gi\|4557485\|ref\|NP__000 | 13 | 19 | 20.90% | 122205 | 5.7 | ceruloplasmin (ferroxidase); Ceruloplasmin [*Homo sapiens*] |
| gi\|4502153\|ref\|NP__000 | 16 | 19 | 6.70% | 515569 | 7.1 | apolipoprotein B precursor apoB-100; apoB-48 [*Homo sapiens*] |

TABLE 1-continued

| | Normal serum GroEL capture | | | | | | |
|---|---|---|---|---|---|---|---|
| DTASelect v1.9 Locus Unique | Sequence Count FileName | Spectrum Count XCorr | Sequence Coverage DeltCN | MolWt CalcM + H+ | pI Total Intensity | Descriptive Name SpScore IonProportion Redundancy Sequence | |
| gi\|22094125\|ref\|NP__06 | 2 | 18 | 4.40% | 98705 | 9.3 | zinc finger protein 28; zinc finger factor X6 [*Homo sapiens*] |
| gi\|41151031\|ref\|XP__37 | 1 | 17 | 39.80% | 10834 | 11.1 | hypothetical protein XP__378771 [*Homo sapiens*] |
| gi\|4503555\|ref\|NP__001 | 2 | 17 | 6.30% | 70730 | 5.6 | E74-like factor 4 (ets domain transcription factor) [*Homo sapiens*] |
| gi\|32484977\|ref\|NP__05 | 1 | 17 | 2.20% | 85835 | 7.3 | angiomotin like 2; Leman coiled-coil protein; angiomotin-like protein 2 [*Homo sapiens*] |
| gi\|22044446\|ref\|XP__08 | 1 | 16 | 4.50% | 41376 | 5.8 | similar to zinc finger, CW-type with PWWP domain 1 [*Homo sapiens*] |
| gi\|17318569\|ref\|NP__00 | 13 | 16 | 27.20% | 66067 | 8.1 | keratin 1; Keratin-1; cytokeratin 1; hair alpha protein [*Homo sapiens*] |
| gi\|38569480\|ref\|NP__05 | 1 | 16 | 1.50% | 114119 | 6 | myocardin-related transcription factor B; megakaryoblastic leukemia 2 [*Homo sapiens*] |
| gi\|22779934\|ref\|NP__07 | 5 | 16 | 8.20% | 151581 | 6.4 | WD repeat membrane protein PWDMP [*Homo sapiens*] |
| gi\|19747267\|ref\|NP__59 | 10 | 16 | 0.50% | 3816051 | 6.3 | titin isoform N2-A; connectin; CMH9, included; cardiomyopathy, dilated 1G (autosomal dominant) [*Homo sapiens*] |
| gi\|7706310\|ref\|NP__057 | 2 | 15 | 8.70% | 47620 | 10 | LUC7-liKe 2; CGI-74 protein; CGI-59 protein; H_NH0792N18.3 [*Homo sapiens*] |
| gi\|42656543\|ref\|XP__37 | 12 | 15 | 4.70% | 722938 | 6.5 | hypothetical protein XP__376158 [*Homo sapiens*] |
| gi\|42661301\|ref\|XP__37 | 1 | 14 | 13.10% | 16384 | 8.7 | hypothetical protein XP__378639 [*Homo sapiens*] |
| gi\|4758148\|ref\|NP__004 | 1 | 14 | 5.10% | 36522 | 4.8 | DNA fragmentation factor, 45 kD, alpha polypeptide; DNA fragmentation factor, 45 kD, alpha subunit; DFF45 [*Homo sapiens*] |
| gi\|4502503\|ref\|NP__000 | 8 | 14 | 12.10% | 67033 | 7.3 | complement component 4 binding protein, alpha; Complement component 4-binding protein, alpha polypeptide; complement component 4-binding protein, alpha [*Homo sapiens*] |
| gi\|29745114\|ref\|XP__29 | 1 | 14 | 1.10% | 75996 | 10.2 | dendrin [*Homo sapiens*] |
| gi\|19923374\|ref\|NP__00 | 6 | 14 | 4.80% | 274881 | 6.9 | human immunodeficiency virus type I enhancer binding protein 2; human immunodeficiency virus type I enhancer-binding protein 2 [*Homo sapiens*] |
| gi\|41146759\|ref\|XP__37 | 3 | 14 | 2.30% | 313978 | 6.8 | odd Oz/Ten-m homolog 3 [*Homo sapiens*] |
| gi\|45439359\|ref\|NP__00 | 6 | 14 | 4.90% | 346901 | 6.4 | triple functional domain (PTPRF interacting) [*Homo sapiens*] |
| gi\|19882213\|ref\|NP__11 | 12 | 14 | 4.60% | 692686 | 4.6 | very large G-protein coupled receptor 1; very large G protein-coupled receptor 1; G protein-coupled receptor 98 [*Homo sapiens*] |
| gi\|41150939\|ref\|XP__37 | 1 | 13 | 19.80% | 10777 | 9.3 | similar to Nonhistone chromosomal protein HMG-14 (High-mobility group nucleosome binding domain 1) [*Homo sapiens*] |
| gi\|38569396\|ref\|NP__00 | 1 | 13 | 10.30% | 24860 | 9.7 | insulin-like 6 precursor; relaxin/insulin-like factor 1; insulin-like peptide 5 [*Homo sapiens*] |
| gi\|4557321\|ref\|NP__000 | 10 | 13 | 31.10% | 30778 | 5.8 | apolipoprotein A-I precursor [*Homo sapiens*] |
| gi\|11276085\|ref\|NP__06 | 1 | 13 | 4.50% | 59941 | 7.9 | UDP glycosyltransferase 1 family, polypeptide A9 [*Homo sapiens*] |
| gi\|4505695\|ref\|NP__002 | 3 | 13 | 8.60% | 63152 | 7.4 | 3-phosphoinositide dependent protein kinase-1; PkB kinase [*Homo sapiens*] |
| gi\|4502193\|ref\|NP__001 | 2 | 13 | 7.10% | 67585 | 9 | v-raf murine sarcoma 3611 viral oncogene homolog 1; Oncogene ARAF1 [*Homo sapiens*] |
| gi\|29731965\|ref\|XP__29 | 7 | 13 | 14.60% | 161753 | 5.6 | KIAA0804 protein [*Homo sapiens*] |
| gi\|5803088\|ref\|NP__005 | 6 | 13 | 7.60% | 181551 | 6.3 | MAP/ERK kinase kinase 4 isoform a; SSK2/SSK22 MAP kinase kinase kinase, yeast, homolog of [*Homo sapiens*] |
| gi\|24308217\|ref\|NP__06 | 8 | 13 | 10.20% | 201300 | 7.6 | KIAA1330 protein [*Homo sapiens*] |
| gi\|42658790\|ref\|XP__37 | 6 | 13 | 6.90% | 232552 | 6.8 | similar to hypothetical protein [*Homo sapiens*] |
| gi\|37541569\|ref\|XP__04 | 11 | 13 | 6.50% | 408536 | 7.7 | zinc finger protein 469 [*Homo sapiens*] |
| gi\|24431966\|ref\|NP__00 | 2 | 12 | 9.30% | 51988 | 5.8 | stress 70 protein chaperone, microsome-associated, 60 kDa; Stress 70 protein chaperone, microsome-associated, p60; human microsomal stress 70 protein ATPase core [*Homo sapiens*] |
| gi\|42741679\|ref\|NP__03 | 2 | 12 | 4.10% | 98082 | 6.6 | ATPase, H+ transporting, lysosomal V0 subunit a isoform 2 [*Homo sapiens*] |
| gi\|21361551\|ref\|NP__00 | 4 | 12 | 10.60% | 137009 | 6.3 | solute carrier family 4, anion exchanger, member 2 (erythrocyte membrane protein band 3-liKe 1) [*Homo sapiens*] |
| gi\|4504375\|ref\|NP__000 | 10 | 12 | 9.10% | 139125 | 6.7 | H factor 1 (complement); H factor-1 (complement); complement factor H; factor H-like 1 [*Homo sapiens*] |
| gi\|4502221\|ref\|NP__001 | 1 | 12 | 1.60% | 171568 | 6.6 | Rho GTPase activating protein 5; RhoGAP5; p190-B [*Homo sapiens*] |
| gi\|41146538\|ref\|XP__29 | 3 | 12 | 3.20% | 235179 | 7.3 | similar to KIAA2018 protein [*Homo sapiens*] |
| gi\|4508019\|ref\|NP__003 | 8 | 12 | 3.30% | 416471 | 7.5 | bassoon; zinc finger protein 231; neuronal double zinc finger protein [*Homo sapiens*] |

TABLE 1-continued

Normal serum GroEL capture

| DTASelect v1.9 Locus Unique | Sequence Count FileName | Spectrum Count XCorr | Sequence Coverage DeltCN | MolWt CalcM + H+ | pI Total Intensity | Descriptive Name SpScore IonProportion Redundancy Sequence |
|---|---|---|---|---|---|---|
| gi\|42661056\|ref\|XP__29 | 2 | 11 | 5.20% | 64976 | 8 | similar to ataxin 2 binding protein 1 isoform gamma; hexaribonucleotide binding protein 1 [*Homo sapiens*] |
| gi\|42476164\|ref\|NP__00 | 1 | 11 | 3.80% | 76472 | 6.8 | POU domain, class 2, transcription factor 1; Octamer-binding transcription factor-1 [*Homo sapiens*] |
| gi\|4502175\|ref\|NP__001 | 2 | 11 | 2.40% | 176409 | 7.1 | apical protein of Xenopus-like; APX homolog of Xenopus [*Homo sapiens*] |
| gi\|4502501\|ref\|NP__000 | 6 | 11 | 4.90% | 192796 | 7.3 | complement component 4B proprotein [*Homo sapiens*] |
| gi\|19718755\|ref\|NP__00 | 2 | 11 | 2.50% | 198839 | 6.4 | RAN-binding protein 2-like 1 isoform 1; sperm membrane protein BS-63; RAN-binding protein 2-like 1 [*Homo sapiens*] |
| gi\|5453571\|ref\|NP__006 | 5 | 11 | 6.10% | 208708 | 5.9 | brefeldin A-inhibited guanine nucleotide-exchange protein 1 [*Homo sapiens*] |
| gi\|20977541\|ref\|NP__06 | 5 | 11 | 5.20% | 217325 | 7.8 | Rho GTPase activating protein 21; Rho-GTPase activating protein 10 [*Homo sapiens*] |
| gi\|33636748\|ref\|NP__07 | 5 | 11 | 4.60% | 278806 | 6 | hypothetical protein FLJ21439 [*Homo sapiens*] |
| gi\|41150991\|ref\|XP__37 | 3 | 11 | 1.70% | 305700 | 8.2 | NYD-SP11 protein [*Homo sapiens*] |
| gi\|21362014\|ref\|NP__07 | 1 | 10 | 3.50% | 79353 | 7.2 | hypothetical protein FLJ22344 [*Homo sapiens*] |
| gi\|42734315\|ref\|NP__05 | 3 | 10 | 3.40% | 90395 | 7.7 | KIAA0317 [*Homo sapiens*] |
| gi\|17978502\|ref\|NP__00 | 7 | 10 | 18.90% | 91819 | 8.7 | alpha 1 type IX collagen isoform 1 precursor; collagen IX, alpha-1 polypeptide; cartilage-specific short collagen [*Homo sapiens*] |
| gi\|4504783\|ref\|NP__002 | 8 | 10 | 16.60% | 106714 | 7 | inter-alpha (globulin) inhibitor, H2 polypeptide [*Homo sapiens*] |
| gi\|18201915\|ref\|NP__54 | 9 | 10 | 16.90% | 159976 | 8.6 | alpha 2 type XI collagen isoform 3 preproprotein [*Homo sapiens*] |
| gi\|41204884\|ref\|XP__03 | 7 | 10 | 4.30% | 396079 | 5.7 | START domain containing 9 [*Homo sapiens*] |
| gi\|42659582\|ref\|XP__37 | 9 | 10 | 5.50% | 485019 | 6.8 | dynein, cytoplasmic, heavy polypeptide 2 [*Homo sapiens*] |
| gi\|31083306\|ref\|NP__11 | 9 | 10 | 3.80% | 613524 | 6.5 | hemicentin; fibulin 6 [*Homo sapiens*] |
| gi\|33188445\|ref\|NP__03 | 5 | 10 | 1.80% | 620426 | 5.4 | microfilament and actin filament cross-linker protein isoform a; 620 kDa actin binding protein; actin cross-linking factor; macrophin 1; trabeculin-alpha; actin cross-lin |
| gi\|6912406\|ref\|NP__036 | 1 | 9 | 6.60% | 32542 | 5.9 | 3-hydroxyanthranilate 3,4-dioxygenase [*Homo sapiens*] |
| gi\|20127446\|ref\|NP__00 | 2 | 9 | 4.40% | 88054 | 6.1 | integrin, beta 5 [*Homo sapiens*] |
| gi\|32526894\|ref\|NP__84 | 3 | 9 | 8.50% | 92537 | 6.7 | hypothetical protein FLJ35834 [*Homo sapiens*] |
| gi\|39930403\|ref\|NP__06 | 2 | 9 | 8.10% | 99267 | 6 | leucine-rich repeat-containing G protein-coupled receptor 6 [*Homo sapiens*] |
| gi\|31543297\|ref\|NP__00 | 2 | 9 | 5.00% | 104372 | 6.2 | neutral sphingomyelinase (N-SMase) activation associated factor [*Homo sapiens*] |
| gi\|4885643\|ref\|NP__005 | 4 | 9 | 7.30% | 111431 | 6 | tumor protein p53 binding protein, 2; apoptosis-stimulating protein of p53, 2 [*Homo sapiens*] |
| gi\|19923493\|ref\|NP__06 | 6 | 9 | 10.50% | 127464 | 7.5 | phosphoinositol 3-phosphate-binding protein-2 [*Homo sapiens*] |
| gi\|24850456\|ref\|NP__05 | 2 | 9 | 4.30% | 128820 | 8.4 | SMC5 protein [*Homo sapiens*] |
| gi\|7706513\|ref\|NP__057 | 1 | 9 | 1.60% | 137136 | 6.3 | PDZ domain-containing guanine nucleotide exchange factor I; rap guanine nucleotide exchange factor; PDZ domain containing guanine nucleotide exchange factor (GEF) 2 [*Homo sapiens*] |
| gi\|4885399\|ref\|NP__005 | 4 | 9 | 5.60% | 141541 | 7.2 | chondroitin sulfate proteoglycan 6 (bamacan); human chromosome-associated polypeptide (bamacan); SMC3 structural maintenance of chromosomes 3-like 1 (yeast) [*Homo sapiens*] |
| gi\|42659545\|ref\|XP__37 | 6 | 9 | 6.40% | 196409 | 5.7 | ankyrin repeat domain 26 [*Homo sapiens*] |
| gi\|39652624\|ref\|NP__03 | 9 | 9 | 10.60% | 233152 | 7.4 | extra spindle poles like 1 [*Homo sapiens*] |
| gi\|38202219\|ref\|NP__07 | 2 | 9 | 1.50% | 240001 | 6.7 | hypothetical protein FLJ12178 [*Homo sapiens*] |

TABLE 2

Normal serum Gel Filtration

| DTASelect v1.9 Locus | Sequence Count | Spectrum Count | Sequence Coverage | MolWt | pI | Descriptive Name |
|---|---|---|---|---|---|---|
| gi\|4502027\|ref\|NP__000 | 109 | 1439 | 81.10% | 69367 | 6.3 | albumin precursor PRO0883 protein [*Homo sapiens*] |
| gi\|4557385\|ref\|NP__000 | 62 | 90 | 47.10% | 187163 | 6.4 | complement component 3 precursor; acylation-stimulating protein cleavage product [*Homo sapiens*] |
| gi\|4557225\|ref\|NP__000 | 55 | 85 | 48.80% | 163277 | 6.4 | alpha 2 macroglobulin precursor [*Homo sapiens*] |
| gi\|4557871\|ret\|NP__001 | 33 | 67 | 56.60% | 77050 | 7.1 | transferrin; PRO2086 protein [*Homo sapiens*] |
| gi\|4557321\|ref\|NP__000 | 25 | 57 | 46.80% | 30778 | 5.8 | apolipoprotein A-I precursor [*Homo sapiens*] |

TABLE 2-continued

| | Normal serum Gel Filtration | | | | | |
|---|---|---|---|---|---|---|
| DTASelect v1.9 Locus | Sequence Count | Spectrum Count | Sequence Coverage | MolWt | pI | Descriptive Name |
| gi|21361198|ref|NP_00 | 20 | 49 | 40.20% | 46723 | 5.6 | serine (or cysteine) proteinase inhibitor, clade A (alpha-1 antiproteinase, antitrypsin), member 1; Protease inhibitor (alpha-1-antitrypsin); protease inhibitor 1 (anti-e |
| gi|11321561|ref|NP_00 | 23 | 37 | 49.60% | 51676 | 7 | hemopexin [Homo sapiens] |
| gi|32483410|ref|NP_00 | 22 | 35 | 48.70% | 52918 | 5.4 | vitamin D-binding protein precursor; vitamin D-binding alpha-globulin [Homo sapiens] |
| gi|4502149|ref|NP_001 | 6 | 31 | 43.00% | 11175 | 6.6 | apolipoprotein A-II precursor [Homo sapiens] |
| gi|4502501|ref|NP_000 | 24 | 31 | 21.70% | 192796 | 7.3 | complement component 4B proprotein [Homo sapiens] |
| gi|4826762|ref|NP_005 | 12 | 28 | 44.60% | 45205 | 6.6 | haptoglobin [Homo sapiens] |
| gi|4557485|ref|NP_000 | 22 | 26 | 31.20% | 122205 | 5.7 | ceruloplasmin (ferroxidase); Ceruloplasmin [Homo sapiens] |
| gi|4504253|ref|NP_002 | 4 | 23 | 33.60% | 15145 | 10.7 | H2A histone family, member X; H2AX histone [Homo sapiens] |
| gi|4504255|ref|NP_002 | 3 | 22 | 25.00% | 13553 | 10.6 | H2A histone family, member Z; H2AZ histone [Homo sapiens] |
| gi|31542984|ref|NP_00 | 16 | 20 | 27.80% | 103357 | 7 | inter-alpha (globulin) inhibitor H4 (plasma Kallikrein-sensitive glycoprotein); inter-alpha (globulin) inhibitor, H polypeptide-like 1; Inter-alpha (globulin) inhibitor, |
| gi|4504783|ref|NP_002 | 14 | 20 | 23.40% | 106714 | 7 | inter-alpha (globulin) inhibitor, H2 polypeptide [Homo sapiens] |
| gi|21264330|ref|NP_54 | 1 | 18 | 2.00% | 109909 | 8.4 | skeletrophin; novelzin [Homo sapiens] |
| gi|4504165|ref|NP_000 | 11 | 17 | 24.80% | 85697 | 6.3 | gelsolin isoform a [Homo sapiens] |
| gi|4502153|ref|NP_000 | 15 | 17 | 5.90% | 515569 | 7.1 | apolipoprotein B precursor; apoB-100; apoB-48 [Homo sapiens] |
| gi|41203848|ref|XP_37 | 5 | 15 | 14.30% | 84926 | 4.8 | similar to Ig alpha-2 chain C region [Homo sapiens] |
| gi|4557327|ref|NP_000 | 12 | 14 | 29.60% | 38312 | 8 | beta-2-glycoprotein I precursor [Homo sapiens] |
| gi|4502151|ref|NP_000 | 10 | 14 | 29.50% | 45381 | 5.4 | apolipoprotein A-IV precursor [Homo sapiens] |
| gi|4502397|ref|NP_001 | 13 | 14 | 20.00% | 85505 | 7 | complement factor B preproprotein; C3 proactivator; C3 proaccelerator; glycine-rich beta-glycoprotein; C3/C5 convertase [Homo sapiens] |
| gi|4502005|ref|NP_001 | 10 | 13 | 41.70% | 39325 | 5.7 | alpha-2-HS-glycoprotein; Alpha-2HS-glycoprotein [Homo sapiens] |
| gi|41150283|ref|XP_05 | 2 | 13 | 3.50% | 146662 | 5.3 | KIAA1005 protein [Homo sapiens] |
| gi|9257232|ref|NP_000 | 9 | 12 | 32.30% | 23512 | 5 | orosomucoid 1 precursor; Orosomucoid-1 (alpha-1-acid glycoprotein-1); alpha-1-acid glycoprotein 1 [Homo sapiens] |
| gi|4505881|ref|NP_000 | 11 | 12 | 27.90% | 90569 | 7.2 | plasminogen [Homo sapiens] |
| gi|21071030|ref|NP_57 | 9 | 11 | 32.10% | 54254 | 5.9 | alpha 1B-glycoprotein [Homo sapiens] |
| gi|4503635|ref|NP_000 | 9 | 11 | 19.10% | 70037 | 5.9 | coagulation factor II precursor; prothrombin [Homo sapiens] |
| gi|4504375|ref|NP_000 | 10 | 11 | 12.30% | 139125 | 6.7 | H factor 1 (complement); H factor-1 (complement); complement factor H; factor H-like 1 [Homo sapiens] |
| gi|4503481|ref|NP_001 | 3 | 10 | 5.70% | 50119 | 6.7 | eukaryotic translation elongation factor 1 gamma; elongation factor 1-gamma; EF-1-gamma; eEF-1B gamma; translation elongation factor eEF-1 gamma chain; PRO1608; pancreatic |
| gi|18201911|ref|NP_00 | 4 | 10 | 10.90% | 54336 | 5.8 | vitronectin precursor; serum spreading factor; somatomedin B; complement S-protein; epibolin [Homo sapiens] |
| gi|4504781|ref|NP_002 | 10 | 10 | 22.20% | 101402 | 6.8 | inter-alpha (globulin) inhibitor, H1 polypeptide [Homo sapiens] |
| gi|4504289|ref|NP_003 | 1 | 9 | 23.50% | 15404 | 11.1 | H3 histone family, member F [Homo sapiens] |
| gi|5174411|ref|NP_005 | 8 | 9 | 32.00% | 38088 | 5.5 | CD5 antigen-like (scavenger receptor cysteine rich family); Spalpha [Homo sapiens] |
| gi|5902134|ref|NP_009 | 1 | 9 | 3.00% | 51026 | 6.7 | coronin, actin binding protein, 1A; coronin, actin-binding, 1A; coronin, actin-binding protein, 1A; coronin-1 [Homo sapiens] |
| gi|29336063|ref|NP_00 | 1 | 9 | 0.70% | 206846 | 6.4 | plexin B3; plexin 6; plexin-B3 [Homo sapiens] |
| gi|4557323|ref|NP_000 | 5 | 8 | 20.20% | 10852 | 5.4 | apolipoprotein C-III precursor [Homo sapiens] |
| gi|4507621|ref|NP_003 | 1 | 8 | 9.90% | 21338 | 8.7 | troponin I, skeletal, fast; Troponin I fast twitch 2; Troponin I, fast-twitch skeletal muscle isoform [Homo sapiens] |
| gi|7669492|ref|NP_002 | 3 | 8 | 22.40% | 36053 | 8.5 | glyceraldehyde-3-phosphate dehydrogenase [Homo sapiens] |
| gi|4758496|ref|NP_004 | 1 | 8 | 7.80% | 39489 | 9.8 | H2A histone family, member Y isoform 2; histone macroH2A1.2; histone macroH2A1.1 [Homo sapiens] |
| gi|4501843|ref|NP_001 | 6 | 8 | 19.60% | 48637 | 6.2 | alpha-1-antichymotrypsin, precursor; alpha-1-antichymotrypsin; antichymotrypsin [Homo sapiens] |
| gi|17318569|ref|NP_00 | 5 | 8 | 14.80% | 66067 | 8.1 | keratin 1; Keratin-1; cytokeratin 1; hair alpha protein [Homo sapiens] |
| gi|32307124|ref|NP_00 | 1 | 8 | 1.50% | 154891 | 7.5 | nuclear receptor coactivator 3 isoform b; amplified in breast cancer-1; thyroid hormone receptor activator molecule 1; receptor-associated coactivator 3; steroid receptor |
| gi|38016947|ref|NP_00 | 7 | 8 | 4.50% | 188304 | 6.5 | complement component 5 [Homo sapiens] |
| gi|10947052|ref|NP_00 | 3 | 8 | 1.10% | 433749 | 5.1 | ankyrin 2 isoform 1; ankyrin-2, nonerythrocytic; ankyrin-B; ankyrin, brain; ankyrin, neuronal; |

TABLE 2-continued

| | Normal serum Gel Filtration | | | | | |
|---|---|---|---|---|---|---|
| DTASelect v1.9 Locus | Sequence Count | Spectrum Count | Sequence Coverage | MolWt | pI | Descriptive Name |
| | | | | | | ankyrin, nonerythroid; Long QT syndrome-4; long (electrocardiographic) QT s |
| gi\|4505409\|ref\|NP_002 | 2 | 7 | 7.20% | 17298 | 8.4 | nucleoside-diphosphate kinase 2; non-metastatic cells 2, protein (NM23) expressed in; c-myc transcription factor [*Homo sapiens*] |
| gi\|4507949\|ref\|NP_003 | 1 | 7 | 8.10% | 28082 | 4.8 | tyrosine 3-monooxygenase/tryptophan 5-monooxygenase activation protein, beta polypeptide; 14-3-3 protein beta/alpha; protein kinase C inhibitor protein-1; protein 1054; br |
| gi\|4504893\|ref\|NP_000 | 5 | 7 | 16.20% | 47883 | 6.7 | kininogen [*Homo sapiens*] |
| gi\|4502261\|ref\|NP_000 | 6 | 7 | 13.40% | 52602 | 6.7 | serine (or cysteine) proteinase inhibitor, clade C (antithrombin), member 1; antithrombin III [*Homo sapiens*] |
| gi\|4502503\|ref\|NP_000 | 6 | 7 | 14.70% | 67033 | 7.3 | complement component 4 binding protein, alpha; Complement component 4-binding protein, alpha polypeptide; complement component 4-binding protein, alpha [*Homo sapiens*] |
| gi\|4502493\|ref\|NP_001 | 5 | 7 | 13.60% | 80200 | 6.3 | complement component 1, r subcomponent [*Homo sapiens*] |
| gi\|40254816\|ref\|NP_00 | 3 | 7 | 7.40% | 84674 | 5 | heat shock 90 kDa protein 1, alpha; heat shock 90 kD protein 1, alpha [*Homo sapiens*] |
| gi\|4504347\|ref\|NP_000 | 6 | 6 | 60.60% | 15258 | 8.7 | alpha 1 globin [*Homo sapiens*] |
| gi\|28872725\|ref\|NP_00 | 1 | 6 | 3.60% | 47464 | 6.5 | proteasome 26S non-ATPase subunit 11; 26S proteasome regulatory subunit 9 [*Homo sapiens*] |
| gi\|4557287\|ref\|NP_000 | 4 | 6 | 16.30% | 53154 | 6.3 | angiotensinogen precursor; pre-angiotensinogen; angiotensin I [*Homo sapiens*] |
| gi\|31377715\|ref\|NP_07 | 2 | 6 | 7.60% | 66841 | 8.3 | solute carrier family 13 member 3; sodium-dependent high affinity dicarboxylate transporter 3; Na(+)/dicarboxylate cotransporter 3 [*Homo sapiens*] |
| gi\|21735575\|ref\|NP_06 | 1 | 6 | 3.50% | 71686 | 9.3 | junctophilin 1; mitsugumin72; junctophilin type1 [*Homo sapiens*] |
| gi\|5032135\|ref\|NP_005 | 2 | 6 | 1.20% | 174258 | 7.4 | ATP-binding cassette, sub-family C, member 9 isoform SUR2A; sulfonylurea receptor 2A [*Homo sapiens*] |
| gi\|42661087\|ref\|XP_08 | 1 | 6 | 0.40% | 446640 | 6.5 | FLJ46675 protein [*Homo sapiens*] |
| gi\|27484057\|ref\|XP_21 | 2 | 5 | 22.20% | 12427 | 6.6 | hypothetical protein XP_211339 [*Homo sapiens*] |
| gi\|11036646\|ref\|NP_05 | 2 | 5 | 18.30% | 13944 | 10.4 | H2B histone family, member S [*Homo sapiens*] |
| gi\|42661381\|ref\|XP_37 | 1 | 5 | 10.90% | 19331 | 8.3 | hypothetical protein XP_378743 [*Homo sapiens*] |
| gi\|5803139\|ref\|NP_006 | 5 | 5 | 42.20% | 22868 | 5.7 | RBP4 gene product [*Homo sapiens*] |
| gi\|4557325\|ref\|NP_000 | 5 | 5 | 17.40% | 36154 | 5.7 | apolipoprotein E [*Homo sapiens*] |
| gi\|19923106\|ref\|NP_00 | 5 | 5 | 22.00% | 39731 | 5.2 | paraoxonase 1; Paraoxonase [*Homo sapiens*] |
| gi\|4502595\|ref\|NP_001 | 3 | 5 | 6.40% | 45141 | 6 | corticosteroid binding globulin precursor; corticosteroid binding globulin; alpha-1 antiproteinase, antitrypsin [*Homo sapiens*] |
| gi\|4506801\|ref\|NP_003 | 1 | 5 | 4.10% | 70869 | 4.8 | secretogranin II precursor; Chromogranin C (secretogranin II); secretoneurin precursor; EM66 precursor [*Homo sapiens*] |
| gi\|20149594\|ref\|NP_03 | 1 | 5 | 3.70% | 83264 | 5 | heat shock 90 kDa protein 1, beta; heat shock 90 kD protein 1, beta; Heat-shock 90 kD protein-1, beta [*Homo sapiens*] |
| gi\|42662523\|ref\|XP_37 | 2 | 5 | 2.20% | 130322 | 6.8 | zinc finger, BED domain containing 4 [*Homo sapiens*] |
| gi\|15451892\|ref\|NP_05 | 1 | 5 | 0.80% | 138929 | 5.5 | translation initiation factor IF2 [*Homo sapiens*] |
| gi\|45439327\|ref\|NP_00 | 3 | 5 | 3.40% | 204676 | 5.6 | periplakin; 195 kDa cornified envelope precursor; 190 kDa paraneoplastic pemphigus antigen [*Homo sapiens*] |
| gi\|20143922\|ref\|NP_59 | 4 | 5 | 0.30% | 3E+06 | 6.7 | titin isoform novex-2; connectin; CMH9, included; cardiomyopathy, dilated 1G (autosomal dominant) [*Homo sapiens*] |
| gi\|41222847\|ref\|XP_37 | 2 | 4 | 12.10% | 10382 | 9.5 | hypothetical protein XP_378690 [*Homo sapiens*] |
| gi\|41150939\|ref\|XP_37 | 1 | 4 | 19.80% | 10777 | 9.3 | similar to Nonhistone chromosomal protein HMG-14 (High-mobility group nucleosome binding domain 1) [*Homo sapiens*] |
| gi\|24638446\|ref\|NP_00 | 1 | 4 | 22.50% | 13988 | 10.9 | H2A histone family, member Q; H2A histone; histone IIa [*Homo sapiens*] |
| gi\|4507725\|ref\|NP_000 | 3 | 4 | 35.40% | 15887 | 5.7 | transthyretin (prealbumin, amyloidosis type I); Transthyretin (prealbumin) [*Homo sapiens*] |
| gi\|4504349\|ref\|NP_000 | 4 | 4 | 38.80% | 15998 | 7.3 | beta globin [*Homo sapiens*] |
| gi\|42659183\|ref\|XP_37 | 2 | 4 | 14.40% | 20014 | 11.5 | hypothetical protein XP_379629 [*Homo sapiens*] |
| gi\|7705753\|ref\|NP_057 | 3 | 4 | 20.40% | 26017 | 9.1 | complement component 1, q subcomponent, alpha polypeptide precursor; complement component C1q, A chain [*Homo sapiens*] |
| gi\|12056465\|ref\|NP_00 | 1 | 4 | 5.90% | 33784 | 10.2 | fibrillarin; 34-kD nucleolar scleroderma antigen; RNA, U3 small nucleolar interacting protein 1 [*Homo sapiens*] |
| gi\|4502337\|ref\|NP_001 | 4 | 4 | 18.80% | 34259 | 6.1 | alpha-2-glycoprotein 1, zinc; Alpha-2-glycoprotein, zinc [*Homo sapiens*] |
| gi\|11321587\|ref\|NP_00 | 3 | 4 | 30.60% | 37662 | 7.6 | H factor (complement)-like 1 [*Homo sapiens*] |
| gi\|4885049\|ref\|NP_005 | 2 | 4 | 8.20% | 42019 | 5.4 | actin, alpha, cardiac muscle precursor [*Homo sapiens*] |

TABLE 2-continued

| | Normal serum Gel Filtration | | | | | |
|---|---|---|---|---|---|---|
| DTASelect v1.9 Locus | Sequence Count | Spectrum Count | Sequence Coverage | MolWt | pI | Descriptive Name |
| gi\|4503645\|ref\|NP_000 | 2 | 4 | 11.20% | 51594 | 7.2 | coagulation factor VII precursor isoform a; Coagulation factor VII; eptacog alfa [*Homo sapiens*] |
| gi\|39930485\|ref\|NP_44 | 1 | 4 | 3.40% | 52689 | 8.4 | mitochondrial Ca2+-dependent solute carrier [*Homo sapiens*] |
| gi\|4504489\|ref\|NP_000 | 4 | 4 | 13.70% | 59578 | 7.5 | histidine-rich glycoprotein precursor; histidine-proline rich glycoprotein; thrombophilia due to elevated HRG, included [*Homo sapiens*] |
| gi\|4502511\|ref\|NP_001 | 4 | 4 | 11.40% | 63173 | 5.6 | complement component 9 [*Homo sapiens*] |
| gi\|4503629\|ref\|NP_000 | 3 | 4 | 12.40% | 67818 | 7.7 | coagulation factor XII precursor; Hageman factor [*Homo sapiens*] |
| gi\|21361845\|ref\|NP_44 | 4 | 4 | 15.50% | 67970 | 7.7 | peptidoglycan recognition protein L precursor [*Homo sapiens*] |
| gi\|4507429\|ref\|NP_003 | 2 | 4 | 5.10% | 73629 | 8.4 | tec protein tyrosine kinase [*Homo sapiens*] |
| gi\|4502495\|ref\|NP_001 | 3 | 4 | 6.00% | 76685 | 5 | complement component 1, s subcomponent [*Homo sapiens*] |
| gi\|13129040\|ref\|NP_07 | 2 | 4 | 6.60% | 80682 | 8 | spermatogenesis associated 5-like 1 [*Homo sapiens*] |
| gi\|17978489\|ref\|NP_00 | 3 | 4 | 5.80% | 81743 | 7.1 | CD97 antigen isoform 2 precursor; leukocyte antigen CD97; seven-span transmembrane protein [*Homo sapiens*] |
| gi\|31377758\|ref\|NP_06 | 2 | 4 | 7.60% | 99444 | 4.6 | aftiphilin protein isoform 1 [*Homo sapiens*] |
| gi\|14149661\|ref\|NP_05 | 1 | 4 | 2.20% | 108793 | 6.6 | Rab6-interacting protein 2 isoform alpha [*Homo sapiens*] |
| gi\|40805104\|ref\|NP_00 | 1 | 4 | 2.50% | 119198 | 9.5 | topoisomerase I binding, arginine/serine-rich; tumor protein p53-binding protein; topoisomerase I binding protein [*Homo sapiens*] |
| gi\|40786422\|ref\|NP_95 | 3 | 4 | 6.10% | 148944 | 4.9 | dachsous-like [*Homo sapiens*] |
| gi\|4504949\|ref\|NP_002 | 1 | 4 | 0.70% | 201882 | 6.3 | laminin, alpha 4 precursor [*Homo sapiens*] |
| gi\|28872786\|ref\|NP_06 | 1 | 4 | 0.80% | 215035 | 5.6 | CDK5 regulatory subunit associated protein 2; CDK5 activator-binding protein C48 [*Homo sapiens*] |

The invention claimed is:

1. A protein separation device comprising GroEL immobilised on a substrate, wherein the specificity of GroEL is directed to a particular protein, wherein GroEL is engineered by site-directed mutagenesis to have the substitutions, leucine 200 to arginine; serine 201 to glycine, and proline 202 to aspartate.

2. The protein separation device as claimed in claim 1, in which the substitutions introduce an integrin binding motif into a protein binding domain of GroEL.

3. The protein separation device as claimed in claim 1, in which GroEL comprises a back-to-back double ring configuration.

4. The protein separation device as claimed in claim 1, in which GroEL is in operative association with a co-factor.

5. The protein separation device as claimed in claim 4, in which the co-factor is GroES.

6. The protein separation device as claimed in claim 1, in which the chaperone is obtainable from a microbial source selected from the group consisting of *Escherichia* spp., *Thermus* spp. *Streptococcus* spp., *Staphylococcus* spp., *Bacillus* spp., *Leptospira* spp., *Spirillum* spp., *Lactobacillus* spp., *Mycoplasma* spp., *Pseudomonas* spp., *Streptomyces* spp., *Corynebacterium* spp., *Bacteroides* spp. and *Clostridium* spp.

7. The protein separation device as claimed in claim 6, in which the *Escherichia* spp. microbial source is *Escherichia coli*.

8. The protein separation device as claimed in claim 1, in which the substrate is a solid support of the array or bead type.

9. The protein separation device as claimed in claim 1, in which the substrate is manufactured from a plastics material.

10. The protein separation device as claimed in claim 1, in which the support of the array type is provided with a surface for immobilisation of a protein of the chaperone type thereon.

11. The protein separation device as claimed in claim 10, in which the surface is comprised of moieties selected from the group consisting of nitriloacetic acid, avidin, streptavidin, carboxylates, quaternary amines, silicates, carbonyl diimidazoles and epoxides.

12. The protein separation device as claimed in claim 10, in which the surface is provided with an hydrophobic barrier coating.

13. The protein separation device as claimed in claim 1, in which said protein is separated from a biological sample selected from the group consisting of cerebrospinal fluid, urine and nipple aspirant.

14. The protein separation device as claimed in claim 1, in which said protein is separated from a biological fluid or extract.

15. The protein separation device as claimed in claim 1, in which said protein is separated from a biological sample which has been denatured.

16. A protein separation device comprising GroEL immobilised on a substrate, wherein the specificity of GroEL is changed to a protein specificity of another chaperone protein, in which GroEL is engineered by site-directed mutagenesis to have the substitutions, Tyrosine 199 to Isoleucine; Tyrosine 204 to Isoleucine; Leucine 234 to Isoleucine; Leucine 237 to Isoleucine; Leucine 259 to Phenylalanine; Valine 263 to Leucine and Valine 264 to Phenyalanine.

17. The protein separation device as claimed in claim 16, in which the substitutions replace the substrate binding specificity of GroEL, a group I chaperone, with that of thermosome, a group II chaperone.

18. The protein separation device as claimed in claim 16, in which GroEL comprises a back-to-back double ring configuration.

19. The protein separation device as claimed in claim 16, in which GroEL is in operative association with a co-factor.

20. The protein separation device as claimed in claim 19, in which the co-factor is GroES.

21. The protein separation device as claimed in claim 16, in which the chaperone is obtainable from a microbial source selected from the group consisting of *Escherichia* spp., *Thermus* spp. *Streptococcus* spp., *Staphylococcus* spp., *Bacillus* spp., *Leptospira* spp., *Spirillum* spp., *Lactobacillus* spp., *Mycoplasma* spp., *Pseudomonas* spp., *Streptomyces* spp., *Corynebacterium* spp., *Bacteroides* spp. and *Clostridium* spp.

22. The protein separation device as claimed in claim 21, in which the *Escherichia* spp. microbial source is *Escherichia coli*.

23. The protein separation device as claimed in claim 16, in which the substrate is a solid support of the array or bead type.

24. The protein separation device as claimed in claim 23, in which the substrate is manufactured from a plastics material.

25. The protein separation device as claimed in claim 16, in which the support of the array type is provided with a surface for immobilisation of a protein of the chaperone type thereon.

26. The protein separation device as claimed in claim 25, in which the surface is comprised of moieties selected from the group consisting of nitriloacetic acid, avidin, streptavidin, carboxylates, quaternary amines, silicates, carbonyl diimidazoles and epoxides.

27. The protein separation device as claimed in claim 25, in which the surface is provided with an hydrophobic barrier coating.

28. The protein separation device as claimed in claim 18, in which said protein is separated from a biological sample selected from the group consisting of cerebrospinal fluid, urine and nipple aspirant.

29. The protein separation device as claimed in claim 18, in which said protein is separated from a biological fluid or extract.

30. The protein separation device as claimed in claim 18 in which said protein is separated from a biological sample which has been denatured.

* * * * *

SEQUENCE LISTING

```
<160> NUMBER OF SEQ ID NOS: 8

<210> SEQ ID NO 1
<211> LENGTH: 1647
<212> TYPE: DNA
<213> ORGANISM: Escherichia coli
<220> FEATURE:
<221> NAME/KEY: misc_feature
<223> OTHER INFORMATION: GroEL wildtype DNA sequence

<400> SEQUENCE: 1
atggcagcta aagacgtaaa attcggtaac gacgctcgtg tgaaaatgct gcgcggcgta      60
aacgtactgg cagatgcagt gaaagttacc ctcggtccga aaggccgtaa cgtagttctg     120
gataaatctt tcggtgcacc gaccatcacc aaagatggtg tttccgttgc tcgtgaaatc     180
gaactggaag acaagttcga aaacatgggt gcgcagatgg tgaaagaagt tgcctctaaa     240
gcgaacgacg ctgcaggcga cggtaccacc actgcaaccg tactggctca ggctatcatc     300
actgaaggtc tgaaagctgt tgctgcgggc atgaacccga tggacctgaa acgtggtatc     360
gacaaagctg ttaccgctgc agttgaagaa ctgaaagcgc tgtccgtacc gtgctctgac     420
tctaaagcga ttgctcaggt tggtactatc tccgctaact ccgacgaaac cgtaggtaaa     480
ctgatcgctg aagcgatgga caaagtcggt aaagaaggcg ttatcaccgt tgaagacggt     540
accggtctgc aggacgaact ggacgtggtt gaaggtatgc agttcgaccg tggctacctg     600
tctccttact tcatcaacaa gccggaaact ggcgcagtag aactggaaag cccgttcatc     660
ctgctggctg acaagaaaat ctccaacatc cgcgaaatgc tgccggttct ggaagccgtt     720
gccaaagcag gcaaaccgct gctgatcatc gctgaagatg tagaaggcga agcgctggca     780
```

```
actctggttg ttaacaccat gcgtggcatc gtgaaagttg ctgcagttaa agctccgggc    840
ttcggcgatc gtcgtaaagc tatgctgcag gatatcgcaa ccctgactgg cggtaccgta    900
atctctgaag atcggtat ggagctggaa aaagcaaccc tggaagacct gggtcaggct      960
aaacgcgttg tgatcaacaa agacaccacc accatcatcg atggcgtggg cgaagaagct   1020
gcaatccagg ccgtgttgc tcagatccgt cagcagattg aagaagcaac ttctgactac    1080
gaccgtgaaa aactgcagga gcgcgtagcg aaactggcag gcggcgttgc agttatcaaa   1140
gtaggtgctg ctaccgaagt tgaaatgaaa gagaaaaaag cacgcgttga agacgccctg   1200
cacgcgaccc gtgctgcggt agaagaaggc gtggttgctg gtggtggtgt tgcgctgatc   1260
cgcgtagcgt ctaaactggc tgacctgcgt ggtcagaacg aagaccagaa cgtgggtatc   1320
aaagttgcac tgcgtgcaat ggaagctccg ctgcgtcaga tcgtcctgaa ctgcggcgaa   1380
gaaccgtctg ttgttgctaa caccgttaaa ggcggcgacg gcaactacgg ttacaacgca   1440
gcaaccgaag aatacggcaa catgatcgac atgggtatcc tggacccaac caaagtaacc   1500
cgttctgctc tgcagtacgc ggcttctgtg gctggcctga tgatcaccac cgaatgcatg   1560
gttaccgacc tgccgaaaaa cgatgcagct gacttaggcg ctgctggcgg catgggtggc   1620
atgggtggca tgggcggcat gatgtaa                                      1647
```

<210> SEQ ID NO 2
<211> LENGTH: 548
<212> TYPE: PRT
<213> ORGANISM: Escherichia coli
<220> FEATURE:
<221> NAME/KEY: misc_feature
<223> OTHER INFORMATION: GroEL wildtype amino acid sequence

<400> SEQUENCE: 2

```
Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
                20                  25                  30

Pro Lys Gly Arg Asn Val Val Leu Asp Lys Ser Phe Gly Ala Pro Thr
            35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205
```

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 3
<211> LENGTH: 1647
<212> TYPE: DNA
<213> ORGANISM: Escherichia coli
<220> FEATURE:
<221> NAME/KEY: misc_feature
<223> OTHER INFORMATION: GroEL-Asp490Cys DNA sequence
<220> FEATURE:
<221> NAME/KEY: mutation
<222> LOCATION: (1468)..(1470)
<223> OTHER INFORMATION: GAC to TGC -continued

```
<400> SEQUENCE: 3
atggcagcta aagacgtaaa attcggtaac gacgctcgtg tgaaaatgct gcgcggcgta     60
aacgtactgg cagatgcagt gaaagttacc ctcggtccga aaggccgtaa cgtagttctg    120
gataaatctt tcggtgcacc gaccatcacc aaagatggtg tttccgttgc tcgtgaaatc    180
gaactggaag acaagttcga aaacatgggt gcgcagatgg tgaaagaagt tgcctctaaa    240
gcgaacgacg ctgcaggcga cggtaccacc actgcaaccg tactggctca ggctatcatc    300
actgaaggtc tgaaagctgt tgctgcgggc atgaacccga tggacctgaa acgtggtatc    360
gacaaagctg ttaccgctgc agttgaagaa ctgaaagcgc tgtccgtacc gtgctctgac    420
tctaaagcga ttgctcaggt tggtactatc tccgctaact ccgacgaaac cgtaggtaaa    480
ctgatcgctg aagcgatgga caaagtcggt aaagaaggcg ttatcaccgt tgaagacggt    540
accggtctgc aggacgaact ggacgtggtt gaaggtatgc agttcgaccg tggctacctg    600
tctccttact tcatcaacaa gccggaaact ggcgcagtag aactggaaag cccgttcatc    660
ctgctggctg acaagaaaat ctccaacatc cgcgaaatgc tgccggttct ggaagccgtt    720
gccaaagcag caaaccgct gctgatcatc gctgaagatg tagaaggcga agcgctggca    780
actctggttg ttaacaccat gcgtggcatc gtgaaagttg ctgcagttaa agctccgggc    840
ttcggcgatc gtcgtaaagc tatgctgcag gatatcgcaa ccctgactgg cggtaccgta    900
atctctgaag agatcggtat ggagctggaa aaagcaaccc tggaagacct gggtcaggct    960
aaacgcgttg tgatcaacaa agacaccacc accatcatcg atggcgtggg cgaagaagct   1020
gcaatccagg gccgtgttgc tcagatccgt cagcagattg aagaagcaac ttctgactac   1080
gaccgtgaaa aactgcagga gcgcgtagcg aaactggcag gcggcgttgc agttatcaaa   1140
gtaggtgctg ctaccgaagt tgaaatgaaa gagaaaaaag cacgcgttga agacgccctg   1200
cacgcgaccc gtgctgcggt agaagaaggc gtggttgctg gtggtggtgt tgcgctgatc   1260
cgcgtagcgt ctaaactggc tgacctgcgt ggtcagaacg aagaccagaa cgtgggtatc   1320
aaagttgcac tgcgtgcaat ggaagctccg ctgcgtcaga tcgtcctgaa ctgcggcgaa   1380
gaaccgtctg ttgttgctaa caccgttaaa ggcggcgacg gcaactacgg ttacaacgca   1440
gcaaccgaag aatacggcaa catgatctgc atgggtatcc tggacccaac caaagtaacc   1500
cgttctgctc tgcagtacgc ggcttctgtg gctggcctga tgatcaccac cgaatgcatg   1560
gttaccgacc tgccgaaaaa cgatgcagct gacttaggcg ctgctggcgg catgggtggc   1620
atgggtggca tgggcggcat gatgtaa                                       1647
```

<210> SEQ ID NO 4
<211> LENGTH: 548
<212> TYPE: PRT
<213> ORGANISM: Escherichia coli
<220> FEATURE:
<221> NAME/KEY: misc_feature
<223> OTHER INFORMATION: GroEL Asp490Cys amino acid sequence
<220> FEATURE:
<221> NAME/KEY: SITE
<222> LOCATION: (490)..(490)
<223> OTHER INFORMATION: D to C

<400> SEQUENCE: 4

```
Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
```

```
                35                  40                  45
Ile Thr Lys Asp Gly Val Ser Val Ala Arg Glu Ile Glu Leu Glu Asp
 50                  55                  60

Lys Phe Glu Asn Met Gly Ala Gln Met Val Lys Glu Val Ala Ser Lys
 65                  70                  75                  80

Ala Asn Asp Ala Ala Gly Asp Gly Thr Thr Thr Ala Thr Val Leu Ala
                 85                  90                  95

Gln Ala Ile Ile Thr Glu Gly Leu Lys Ala Val Ala Ala Gly Met Asn
                100                 105                 110

Pro Met Asp Leu Lys Arg Gly Ile Asp Lys Ala Val Thr Ala Ala Val
                115                 120                 125

Glu Glu Leu Lys Ala Leu Ser Val Pro Cys Ser Asp Ser Lys Ala Ile
                130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
                180                 185                 190

Met Gln Phe Asp Arg Gly Tyr Leu Ser Pro Tyr Phe Ile Asn Lys Pro
                195                 200                 205

Glu Thr Gly Ala Val Glu Leu Glu Ser Pro Phe Ile Leu Leu Ala Asp
                210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
                260                 265                 270

Val Ala Ala Val Lys Ala Pro Gly Phe Gly Asp Arg Arg Lys Ala Met
                275                 280                 285

Leu Gln Asp Ile Ala Thr Leu Thr Gly Gly Thr Val Ile Ser Glu Glu
                290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
                340                 345                 350

Ile Glu Glu Ala Thr Ser Asp Tyr Asp Arg Glu Lys Leu Gln Glu Arg
                355                 360                 365

Val Ala Lys Leu Ala Gly Gly Val Ala Val Ile Lys Val Gly Ala Ala
                370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
                420                 425                 430

Asn Glu Asp Gln Asn Val Gly Ile Lys Val Ala Leu Arg Ala Met Glu
                435                 440                 445

Ala Pro Leu Arg Gln Ile Val Leu Asn Cys Gly Glu Glu Pro Ser Val
                450                 455                 460
```

```
Val Ala Asn Thr Val Lys Gly Gly Asp Gly Asn Tyr Gly Tyr Asn Ala
465                 470                 475                 480

Ala Thr Glu Glu Tyr Gly Asn Met Ile Cys Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 5
<211> LENGTH: 1647
<212> TYPE: DNA
<213> ORGANISM: Escherichia coli
<220> FEATURE:
<221> NAME/KEY: misc_feature
<223> OTHER INFORMATION: GroEL apical domain RYD modification DNA
      sequence
<220> FEATURE:
<221> NAME/KEY: mutation
<222> LOCATION: (598)..(606)
<223> OTHER INFORMATION: CTGTCTCCT to  CGTTATGAT
<220> FEATURE:
<221> NAME/KEY: mutation
<222> LOCATION: (1468)..(1470)
<223> OTHER INFORMATION: GAC to TGC

<400> SEQUENCE: 5
atggcagcta aagacgtaaa attcggtaac gacgctcgtg tgaaaatgct gcgcggcgta     60
aacgtactgg cagatgcagt gaaagttacc ctcggtccaa aaggccgtaa cgtagttctg    120
gataaatctt tcggtgcacc gaccatcacc aaagatggtg tttccgttgc tcgtgaaatc    180
gaactggaag acaagttcga aaatatgggt gcgcagatgg tgaaagaagt tgcctctaaa    240
gcaaacgacg ctgcaggcga cggtaccacc actgcaaccg tactggctca ggctatcatc    300
actgaaggtc tgaaagctgt tgctgcgggc atgaacccga tggacctgaa acgtggtatc    360
gacaaagcgg ttaccgttgc agttgaagaa ctgaaagcgc tgtccgtacc atgctctgac    420
tctaaagcga ttgctcaggt tggtaccatc tccgctaact ccgacgaaac cgtaggtaaa    480
ctgatcgctg aagcgatgga caaagtcggt aaagaaggcg ttatcaccgt tgaagacggt    540
accggtctgc aggacgaact ggacgtggtt gaaggtatgc agttcgaccg tggctaccgt    600
tatgattact tcatcaacaa gccggaaact ggcgcagtag aactggaaag cccgttcatc    660
ctgctggctg acaagaaaat ctccaacatc cgcgaaatgc tgccggttct ggaagctgtt    720
gccaaagcag gcaaaccgct gctgatcatc gctgaagatg tagaaggcga agcgctggca    780
actctggttg ttaacaccat gcgtggcatc gtgaaagtcg ctgcggttaa agcaccgggc    840
ttcggcgatc gtcgtaaagc tatgctgcag gatatcgcaa ccctgactgg cggtaccgtg    900
atctctgaag atcggtat ggagctggaa aaagcaaccc tggaagacct gggtcaggct    960
aaacgtgttg tgatcaacaa agacaccacc actatcatcg atggcgtggg tgaagaagct    1020
gcaatccagg gccgtgttgc tcagatccgt cagcagattg aagaagcaac ttctgactac    1080
gaccgtgaaa aactgcagga acgcgtagcg aaactggcag cggcgttgc agttatcaaa    1140 gtgggtgctg ctaccgaagt tgaaatgaaa gagaaaaaag cacgcgttga agatgccctg    1200
cacgcgaccc gtgctgcggt agaagaaggc gtggttgctg gtggtggtgt tgcgctgatc    1260
```

```
cgcgtagcgt ctaaactggc tgacctgcgt ggtcagaacg aagaccagaa cgtgggtatc    1320
aaagttgcac tgcgtgcaat ggaagctccg ctgcgtcaga tcgtattgaa ctgcggcgaa    1380
gaaccgtctg ttgttgctaa caccgttaaa ggcggcgacg gcaactacgg ttacaacgca    1440
gcaaccgaag aatacggcaa catgatctgc atgggtatcc tggatccaac caaagtaact    1500
cgttctgctc tgcagtacgc agcttctgtg ctggcctga tgatcaccac cgaatgcatg    1560
gttaccgacc tgccgaaaaa cgatgcagct gacttaggcg ctgctggcgg tatgggcggc    1620
atgggtggca tgggcggcat gatgtaa                                       1647
```

<210> SEQ ID NO 6
<211> LENGTH: 548
<212> TYPE: PRT
<213> ORGANISM: Escherichia coli
<220> FEATURE:
<221> NAME/KEY: misc_feature
<223> OTHER INFORMATION: GroEL apical domain RYD modification
<220> FEATURE:
<221> NAME/KEY: SITE
<222> LOCATION: (200)..(202)
<223> OTHER INFORMATION: LSP to RYD
<220> FEATURE:
<221> NAME/KEY: site
<222> LOCATION: (490)..(490)
<223> OTHER INFORMATION: D to C

<400> SEQUENCE: 6

```
Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Val Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Arg Tyr Asp Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255
```

```
Glu Ala Leu Ala Thr Leu Val Val Asn Thr Met Arg Gly Ile Val Lys
            260                 265                 270
Val Ala Ala Val Lys Ala Pro Gly Phe Gly Asp Arg Arg Lys Ala Met
        275                 280                 285
Leu Gln Asp Ile Ala Thr Leu Thr Gly Gly Thr Val Ile Ser Glu Glu
    290                 295                 300
Ile Gly Met Glu Leu Glu Lys Ala Thr Leu Glu Asp Leu Gly Gln Ala
305                 310                 315                 320
Lys Arg Val Val Ile Asn Lys Asp Thr Thr Thr Ile Ile Asp Gly Val
                325                 330                 335
Gly Glu Glu Ala Ala Ile Gln Gly Arg Val Ala Gln Ile Arg Gln Gln
            340                 345                 350
Ile Glu Glu Ala Thr Ser Asp Tyr Asp Arg Glu Lys Leu Gln Glu Arg
        355                 360                 365
Val Ala Lys Leu Ala Gly Gly Val Ala Val Ile Lys Val Gly Ala Ala
    370                 375                 380
Thr Glu Val Glu Met Lys Glu Lys Lys Ala Arg Val Glu Asp Ala Leu
385                 390                 395                 400
His Ala Thr Arg Ala Ala Val Glu Glu Gly Val Val Ala Gly Gly Gly
                405                 410                 415
Val Ala Leu Ile Arg Val Ala Ser Lys Leu Ala Asp Leu Arg Gly Gln
            420                 425                 430
Asn Glu Asp Gln Asn Val Gly Ile Lys Val Ala Leu Arg Ala Met Glu
        435                 440                 445
Ala Pro Leu Arg Gln Ile Val Leu Asn Cys Gly Glu Glu Pro Ser Val
    450                 455                 460
Val Ala Asn Thr Val Lys Gly Gly Asp Gly Asn Tyr Gly Tyr Asn Ala
465                 470                 475                 480
Ala Thr Glu Glu Tyr Gly Asn Met Ile Cys Met Gly Ile Leu Asp Pro
                485                 490                 495
Thr Lys Val Thr Arg Ser Ala Leu Gln Tyr Ala Ala Ser Val Ala Gly
            500                 505                 510
Leu Met Ile Thr Thr Glu Cys Met Val Thr Asp Leu Pro Lys Asn Asp
        515                 520                 525
Ala Ala Asp Leu Gly Ala Ala Gly Gly Met Gly Gly Met Gly Gly Met
    530                 535                 540
Gly Gly Met Met
545

<210> SEQ ID NO 7
<211> LENGTH: 1647
<212> TYPE: DNA
<213> ORGANISM: Escherichia coli
<220> FEATURE:
<221> NAME/KEY: misc_feature
<223> OTHER INFORMATION: GroEL incorporation of chaperone group II
      apical domain - DNA sequence
<220> FEATURE:
<221> NAME/KEY: mutation
<222> LOCATION: (595)..(597)
<223> OTHER INFORMATION: TAC to ATC
<220> FEATURE:
<221> NAME/KEY: mutation
<222> LOCATION: (607)..(609)
<223> OTHER INFORMATION: TAC to ATC
<220> FEATURE:
<221> NAME/KEY: mutation
<222> LOCATION: (700)..(702)
<223> OTHER INFORMATION: CTG to ATC
<220> FEATURE:
```

```
<221> NAME/KEY: mutation
<222> LOCATION: (709)..(711)
<223> OTHER INFORMATION: CTG to ATC
<220> FEATURE:
<221> NAME/KEY: mutation
<222> LOCATION: (775)..(777)
<223> OTHER INFORMATION: CTG to TTC
<220> FEATURE:
<221> NAME/KEY: mutation
<222> LOCATION: (787)..(792)
<223> OTHER INFORMATION: GTTGTT to CTTTTC
<220> FEATURE:
<221> NAME/KEY: mutation
<222> LOCATION: (1468)..(1470)
<223> OTHER INFORMATION: GAC to TGC

<400> SEQUENCE: 7
atggcagcta aagacgtaaa attcggtaac gacgctcgtg tgaaaatgct gcgcggcgta       60
aacgtactgg cagatgcagt gaaagttacc ctcggtccga aaggccgtaa cgtagttctg      120
gataaatctt tcggtgcacc gaccatcacc aaagatggtt tttccgttgc tcgtgaaatc      180
gaactggaag acaagttcga aaacatgggt gcgcagatgt gaaagaagt tgcctctaaa      240 gcgaacgacg ctgcaggcga cggtaccacc actgcaaccg tactggctca ggctatcatc      300
actgaaggtc tgaaagctgt tgctgcgggc atgaacccga tggacctgaa acgtggtatc      360
gacaaagctg ttaccgctgc agttgaagaa ctgaaagcgc tgtccgtacc gtgctctgac      420
tctaaagcga ttgctcaggt tggtactatc tccgctaact ccgacgaaac cgtaggtaaa      480
ctgatcgctg aagcgatgga caaagtcggt aaagaaggcg ttatcaccgt tgaagacggt      540
accggtctgc aggacgaact ggacgtggtt gaaggtatgc agttcgaccg tggcatcctg      600
tctcctatct tcatcaacaa gccggaaact ggcgcagtag aactggaaag cccgttcatc      660
ctgctggctg acaagaaaat ctccaacatc cgcgaaatga tcccggttat cgaagccgtt      720
gccaaagcag gcaaaccgct gctgatcatc gctgaagatg tagaaggcga agcgttcgca      780
actctgcttt tcaacaccat gcgtggcatc gtgaaagttg ctgcagttaa agctccgggc      840
ttcggcgatc gtcgtaaagc tatgctgcag gatatcgcaa ccctgactgg cggtaccgta      900
atctctgaag agatcggtat ggagctggaa aagcaacccc tggaagacct gggtcaggct      960
aaacgcgttg tgatcaacaa agacaccacc accatcatcg atggcgtggg cgaagaagct     1020
gcaatccagg gccgtgttgc tcagatccgt cagcagattg aagaagcaac ttctgactac     1080
gaccgtgaaa aactgcagga gcgcgtagcg aaactggcag cggcgttgc agttatcaaa     1140 gtaggtgctc taccgaagt tgaaatgaaa gagaaaaaag cacgcgttga agacgccctg     1200
cacgcgaccc gtgctgcggt agaagaaggc gtggttgctg gtggtgtgt tgcgctgatc     1260 cgcgtagcgt ctaaactggc tgacctgcgt ggtcagaacg aagaccagaa cgtgggtatc     1320
aaagttgcac tgcgtgcaat ggaagctccg ctgcgtcaga tcgtcctgaa ctgcggcgaa     1380
gaaccgtctg ttgttgctaa caccgttaaa ggcggcgacg gcaactacgg ttacaacgca     1440
gcaaccgaag aatacggcaa catgatctgc atgggtatcc tggacccaac caaagtaacc     1500
cgttctgctc tgcagtacgc ggcttctgtg gctggcctga tgatcaccac cgaatgcatg     1560
gttaccgacc tgccgaaaaa cgatgcagct gacttaggcg ctgctggcgg catgggtggc     1620
atgggtggca tgggcggcat gatgtaa                                          1647
```

<210> SEQ ID NO 8
<211> LENGTH: 548
<212> TYPE: PRT
<213> ORGANISM: Escherichia coli
<220> FEATURE:

```
<221> NAME/KEY: misc_feature
<223> OTHER INFORMATION: GroEL incorporation of chaperone group II
      apical domain - amino acid sequence
<220> FEATURE:
<221> NAME/KEY: site
<222> LOCATION: (199)..(199)
<223> OTHER INFORMATION: L to I
<220> FEATURE:
<221> NAME/KEY: site
<222> LOCATION: (203)..(203)
<223> OTHER INFORMATION: L to I
<220> FEATURE:
<221> NAME/KEY: site
<222> LOCATION: (234)..(234)
<223> OTHER INFORMATION: L to I
<220> FEATURE:
<221> NAME/KEY: site
<222> LOCATION: (237)..(237)
<223> OTHER INFORMATION: L to I
<220> FEATURE:
<221> NAME/KEY: site
<222> LOCATION: (239)..(239)
<223> OTHER INFORMATION: L to F
<220> FEATURE:
<221> NAME/KEY: site
<222> LOCATION: (263)..(264)
<223> OTHER INFORMATION: VV to LF
<220> FEATURE:
<221> NAME/KEY: site
<222> LOCATION: (490)..(490)
<223> OTHER INFORMATION: D to C

<400> SEQUENCE: 8

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Ile Leu Ser Pro Ile Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Ile Pro Val Ile Glu Ala Val
225                 230                 235                 240

Ala Lys Ala Gly Lys Pro Leu Leu Ile Ile Ala Glu Asp Val Glu Gly
```

```
                        245                 250                 255
Glu Ala Phe Ala Thr Leu Leu Phe Asn Thr Met Arg Gly Ile Val Lys
            260                 265                 270

Val Ala Ala Val Lys Ala Pro Gly Phe Gly Asp Arg Arg Lys Ala Met
            275                 280                 285

Leu Gln Asp Ile Ala Thr Leu Thr Gly Gly Thr Val Ile Ser Glu Glu
            290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
                340                 345                 350

Ile Glu Glu Ala Thr Ser Asp Tyr Asp Arg Glu Lys Leu Gln Glu Arg
            355                 360                 365

Val Ala Lys Leu Ala Gly Gly Val Ala Val Ile Lys Val Gly Ala Ala
            370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
                420                 425                 430

Asn Glu Asp Gln Asn Val Gly Ile Lys Val Ala Leu Arg Ala Met Glu
            435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Cys Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
        530                 535                 540

Gly Gly Met Met
545
```